United States Patent [19]
Jacobs et al.

[11] Patent Number: 5,976,838
[45] Date of Patent: Nov. 2, 1999

[54] SECRETED PROTEINS AND POLYNUCLEOTIDES ENCODING THEM

[75] Inventors: Kenneth Jacobs, Newton; John M. McCoy, Reading; Edward R. LaVallie, Harvard; Lisa A. Racie; David Merberg, both of Acton; Maurice Treacy, Chestnut Hill; Vikki Spaulding, Billerica; Michael J. Agostino, Andover, all of Mass.

[73] Assignee: Genetics Institute, Inc., Cambridge, Mass.

[21] Appl. No.: 08/993,228

[22] Filed: Dec. 18, 1997

Related U.S. Application Data

[63] Continuation-in-part of application No. 08/781,225, Jul. 10, 1997, abandoned, which is a continuation-in-part of application No. 08/769,100, Dec. 18, 1996, abandoned.

[51] Int. Cl.⁶ .................................................. C12N 15/00
[52] U.S. Cl. .................... 435/69.1; 435/91.4; 435/252.3; 435/320.1; 536/23.1; 536/23.5; 530/350
[58] Field of Search .................. 435/69.1, 91.4, 435/252.3, 320.1; 536/23.1, 23.5; 530/350

[56] References Cited

U.S. PATENT DOCUMENTS 5,536,637   7/1996   Jacobs et al. ................................ 435/6

FOREIGN PATENT DOCUMENTS

WO 93/21302   10/1993   WIPO .
WO 96/08510   3/1996    WIPO .

OTHER PUBLICATIONS

Suzuki et al. (1986) An Introduction to Genetic Analysis, Third Ed. WH Freeman and Co. New York, NY, 1986.

Strausberg (1997) GenBank Database, Accession No. AA493985, 1997.

Bultman et al. (1993) GenBank Accession No. A46298, 1993.

Bultman et al. (1992) Cell 71:1195–1204, 1992.

Jacobs et al., Gene 198:289–296, 1997.

Strausberg et al., EMBL EMRST5 Database Accession No. AA493985, Jun. 28, 1997.

*Primary Examiner*—Robert A. Wax
*Assistant Examiner*—Enrique D. Longton
*Attorney, Agent, or Firm*—Hamilton, Brook, Smith & Reynolds, P.C.

[57] ABSTRACT

Novel polynucleotides and the proteins encoded thereby are disclosed.

18 Claims, 2 Drawing Sheets

SECRETED PROTEINS AND POLYNUCLEOTIDES ENCODING THEM

This application is a continuation-in-part of Ser. No. 08/781,225, filed Jan. 10, 1997 now abandoned, which is a continuation-in-part of Ser. No.08/769,100, filed Dec. 18, 1996 and now abandoned, all of which are incorporated by reference herein.

FIELD OF THE INVENTION

The present invention provides novel polynucleotides and proteins encoded by such polynucleotides, along with therapeutic, diagnostic and research utilities for these polynucleotides and proteins.

BACKGROUND OF THE INVENTION

Technology aimed at the discovery of protein factors (including e.g., cytokines, such as lymphokines, interferons, CSFs and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization cloning techniques, have advanced the state of the art by making available large numbers of DNA/amino acid sequences for proteins that are known to have biological activity by virtue of their secreted nature in the case of leader sequence cloning, or by virtue of the cell or tissue source in the case of PCR-based techniques. It is to these proteins and the polynucleotides encoding them that the present invention is directed.

SUMMARY OF THE INVENTION

In one embodiment, the present invention provides a composition comprising an isolated polynucleotide selected from the group consisting of:

(a) a polynucleotide comprising the nucleotide sequence of SEQ ID NO:1;

(b) a polynucleotide comprising the nucleotide sequence of SEQ ID NO:1 from nucleotide 918 to nucleotide 1262;

(c) a polynucleotide comprising the nucleotide sequence of SEQ ID NO:1 from nucleotide 999 to nucleotide 1262;

(d) a polynucleotide comprising the nucleotide sequence of SEQ ID NO:1 from nucleotide 928 to nucleotide 1134;

(e) a polynucleotide comprising the nucleotide sequence of the full-length protein coding sequence of clone AM666_1 deposited under accession number ATCC 98292;

(f) a polynucleotide encoding the full-length protein encoded by the cDNA insert of clone AM666_1 deposited under accession number ATCC 98292;

(g) a polynucleotide comprising the nucleotide sequence of the mature protein coding sequence of clone AM666_1 deposited under accession number ATCC 98292;

(h) a polynucleotide encoding the mature protein encoded by the cDNA insert of clone AM666_1 deposited under accession number ATCC 98292;

(i) a polynucleotide encoding a protein comprising the amino acid sequence of SEQ ID NO:2;

(j) a polynucleotide encoding a protein comprising a fragment of the amino acid sequence of SEQ ID NO:2 having biological activity;

(k) a polynucleotide which is an allelic variant of a polynucleotide of (a)–(h) above;

(l) a polynucleotide which encodes a species homologue of the protein of (i) or (j) above; and (m) a polynucleotide capable of hybridizing under stringent conditions to any one of the polynucleotides specified in (a)–(j).

Preferably, such polynucleotide comprises the nucleotide sequence of SEQ ID NO:1 from nucleotide 918 to nucleotide 1262; the nucleotide sequence of SEQ ID NO:1 from nucleotide 999 to nucleotide 1262; the nucleotide sequence of SEQ ID NO:1 from nucleotide 928 to nucleotide 1134; the nucleotide sequence of the full-length protein coding sequence of clone AM666_1 deposited under accession number ATCC 98292; or the nucleotide sequence of the mature protein coding sequence of clone AM666_1 deposited under accession number ATCC 98292. In other preferred embodiments, the polynucleotide encodes the full-length or mature protein encoded by the cDNA insert of clone AM666_1 deposited under accession number ATCC 98292. In yet other preferred embodiments, the present invention provides a polynucleotide encoding a protein comprising the amino acid sequence of SEQ ID NO:2 from amino acid 5 to amino acid 72.

Other embodiments provide the gene corresponding to the cDNA sequence of SEQ ID NO:1.

In other embodiments, the present invention provides a composition comprising a protein, wherein said protein comprises an amino acid sequence selected from the group consisting of:

(a) the amino acid sequence of SEQ ID NO:2;

(b) the amino acid sequence of SEQ ID NO:2 from amino acid 5 to amino acid 72;

(c) fragments of the amino acid sequence of SEQ ID NO:2; and (d) the amino acid sequence encoded by the cDNA insert of clone AM666_1 deposited under accession number ATCC 98292;

the protein being substantially free from other mammalian proteins. Preferably such protein comprises the amino acid sequence of SEQ ID NO:2 or the amino acid sequence of SEQ ID NO:2 from amino acid 5 to amino acid 72.

In one embodiment, the present invention provides a composition comprising an isolated polynucleotide selected from the group consisting of:

(a) a polynucleotide comprising the nucleotide sequence of SEQ ID NO:3;

(b) a polynucleotide comprising the nucleotide sequence of SEQ ID NO:3 from nucleotide 751 to nucleotide 906;

(c) a polynucleotide comprising the nucleotide sequence of SEQ ID NO:3 from nucleotide 829 to nucleotide 906;

(d) a polynucleotide comprising the nucleotide sequence of SEQ ID NO:3 from nucleotide 556 to nucleotide 831;

(e) a polynucleotide comprising the nucleotide sequence of the full-length protein coding sequence of clone BN387_3 deposited under accession number ATCC 98292;

(f) a polynucleotide encoding the full-length protein encoded by the cDNA insert of clone BN387_3 deposited under accession number ATCC 98292;

(g) a polynucleotide comprising the nucleotide sequence of the mature protein coding sequence of clone BN387_3 deposited under accession number ATCC 98292;

(h) a polynucleotide encoding the mature protein encoded by the cDNA insert of clone BN387_3 deposited under accession number ATCC 98292;

(i) a polynucleotide encoding a protein comprising the amino acid sequence of SEQ ID NO:4;

(j) a polynucleotide encoding a protein comprising a fragment of the amino acid sequence of SEQ ID NO:4 having biological activity;

(k) a polynucleotide which is an allelic variant of a polynucleotide of (a)–(h) above;

(l) a polynucleotide which encodes a species homologue of the protein of (i) or (j) above; and (m) a polynucleotide capable of hybridizing under stringent conditions to any one of the polynucleotides specified in (a)–(j).

Preferably, such polynucleotide comprises the nucleotide sequence of SEQ ID NO:3 from nucleotide 751 to nucleotide 906; the nucleotide sequence of SEQ ID NO:3 from nucleotide 829 to nucleotide 906; the nucleotide sequence of SEQ ID NO:3 from nucleotide 556 to nucleotide 831; the nucleotide sequence of the full-length protein coding sequence of clone BN387_3 deposited under accession number ATCC 98292; or the nucleotide sequence of the mature protein coding sequence of clone BN387_3 deposited under accession number ATCC 98292. In other preferred embodiments, the polynucleotide encodes the full-length or mature protein encoded by the cDNA insert of clone BN387_3 deposited under accession number ATCC 98292. In yet other preferred embodiments, the present invention provides a polynucleotide encoding a protein comprising the amino acid sequence of SEQ ID NO:4 from amino acid 1 to amino acid 27.

Other embodiments provide the gene corresponding to the cDNA sequence of SEQ ID NO:3.

In other embodiments, the present invention provides a composition comprising a protein, wherein said protein comprises an amino acid sequence selected from the group consisting of:

(a) the amino acid sequence of SEQ ID NO:4;

(b) the amino acid sequence of SEQ ID NO:4 from amino acid 1 to amino acid 27;

(c) fragments of the amino acid sequence of SEQ ID NO:4; and (d) the amino acid sequence encoded by the cDNA insert of clone BN387_3 deposited under accession number ATCC 98292;

the protein being substantially free from other mammalian proteins. Preferably such protein comprises the amino acid sequence of SEQ ID NO:4 or the amino acid sequence of SEQ ID NO:4 from amino acid 1 to amino acid 27.

In one embodiment, the present invention provides a composition comprising an isolated polynucleotide selected from the group consisting of:

(a) a polynucleotide comprising the nucleotide sequence of SEQ ID NO:5;

(b) a polynucleotide comprising the nucleotide sequence of SEQ ID NO:5 from nucleotide 139 to nucleotide 765;

(c) a polynucleotide comprising the nucleotide sequence of SEQ ID NO:5 from nucleotide 1 to nucleotide 416;

(d) a polynucleotide comprising the nucleotide sequence of the full-length protein coding sequence of clone BQ135_2 deposited under accession number ATCC 98292;

(e) a polynucleotide encoding the full-length protein encoded by the cDNA insert of clone BQ135_2 deposited under accession number ATCC 98292;

(f) a polynucleotide comprising the nucleotide sequence of the mature protein coding sequence of clone BQ135_2 deposited under accession number ATCC 98292;

(g) a polynucleotide encoding the mature protein encoded by the cDNA insert of clone BQ135_2 deposited under accession number ATCC 98292;

(h) a polynucleotide encoding a protein comprising the amino acid sequence of SEQ ID NO:6;

(i) a polynucleotide encoding a protein comprising a fragment of the amino acid sequence of SEQ ID NO:6 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:5 from nucleotide 139 to nucleotide 765; the nucleotide sequence of SEQ ID NO:5 from nucleotide 1 to nucleotide 416; the nucleotide sequence of the full-length protein coding sequence of clone BQ135_2 deposited under accession number ATCC 98292; or the nucleotide sequence of the mature protein coding sequence of clone BQ135_2 deposited under accession number ATCC 98292. In other preferred embodiments, the polynucleotide encodes the full-length or mature protein encoded by the cDNA insert of clone BQ135_2 deposited under accession number ATCC 98292. In yet other preferred embodiments, the present invention provides a polynucleotide encoding a protein comprising the amino acid sequence of SEQ ID NO:6 from amino acid 1 to amino acid 93.

Other embodiments provide the gene corresponding to the cDNA sequence of SEQ ID NO:5.

In other embodiments, the present invention provides a composition comprising a protein, wherein said protein comprises an amino acid sequence selected from the group consisting of:

(a) the amino acid sequence of SEQ ID NO:6;

(b) the amino acid sequence of SEQ ID NO:6 from amino acid 1 to amino acid 93;

(c) fragments of the amino acid sequence of SEQ ID NO:6; and (d) the amino acid sequence encoded by the cDNA insert of clone BQ135_2 deposited under accession number ATCC 98292;

the protein being substantially free from other mammalian proteins. Preferably such protein comprises the amino acid sequence of SEQ ID NO:6 or the amino acid sequence of SEQ ID NO:6 from amino acid 1 to amino acid 93.

In one embodiment, the present invention provides a composition comprising an isolated polynucleotide selected from the group consisting of:

(a) a polynucleotide comprising the nucleotide sequence of SEQ ID NO:7;

(b) a polynucleotide comprising the nucleotide sequence of SEQ ID NO:7 from nucleotide 214 to nucleotide 714;

(c) a polynucleotide comprising the nucleotide sequence of SEQ ID NO:7 from nucleotide 151 to nucleotide 531;

(d) a polynucleotide comprising the nucleotide sequence of the full-length protein coding sequence of clone CR678_1 deposited under accession number ATCC 98292;

(e) a polynucleotide encoding the full-length protein encoded by the cDNA insert of clone CR678_1 deposited under accession number ATCC 98292;

(f) a polynucleotide comprising the nucleotide sequence of the mature protein coding sequence of clone CR678_1 deposited under accession number ATCC 98292;

(g) a polynucleotide encoding the mature protein encoded by the cDNA insert of clone CR678_1 deposited under accession number ATCC 98292;

(h) a polynucleotide encoding a protein comprising the amino acid sequence of SEQ ID NO:8;

(i) a polynucleotide encoding a protein comprising a fragment of the amino acid sequence of SEQ ID NO:8 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:7 from nucleotide 214 to nucleotide 714; the nucleotide sequence of SEQ ID NO:7 from nucleotide 151 to nucleotide 531; the nucleotide sequence of the full-length protein coding sequence of clone CR678_1 deposited under accession number ATCC 98292; or the nucleotide sequence of the mature protein coding sequence of clone CR678_1 deposited under accession number ATCC 98292. In other preferred embodiments, the polynucleotide encodes the full-length or mature protein encoded by the cDNA insert of clone CR678_1 deposited under accession number ATCC 98292. In yet other preferred embodiments, the present invention provides a polynucleotide encoding a protein comprising the amino acid sequence of SEQ ID NO:8 from amino acid 1 to amino acid 106.

Other embodiments provide the gene corresponding to the cDNA sequence of SEQ ID NO:7.

In other embodiments, the present invention provides a composition comprising a protein, wherein said protein comprises an amino acid sequence selected from the group consisting of:

(a) the amino acid sequence of SEQ ID NO:8;

(b) the amino acid sequence of SEQ ID NO:8 from amino acid 1 to amino acid 106;

(c) fragments of the amino acid sequence of SEQ ID NO:8; and (d) the amino acid sequence encoded by the cDNA insert of clone CR678_1 deposited under accession number ATCC 98292;

the protein being substantially free from other mammalian proteins. Preferably such protein comprises the amino acid sequence of SEQ ID NO:8 or the amino acid sequence of SEQ ID NO:8 from amino acid 1 to amino acid 106.

In one embodiment, the present invention provides a composition comprising an isolated polynucleotide selected from the group consisting of:

(a) a polynucleotide comprising the nucleotide sequence of SEQ ID NO:9;

(b) a polynucleotide comprising the nucleotide sequence of SEQ ID NO:9 from nucleotide 116 to nucleotide 4498;

(c) a polynucleotide comprising the nucleotide sequence of SEQ ID NO:9 from nucleotide 1221 to nucleotide 1711;

(d) a polynucleotide comprising the nucleotide sequence of the full-length protein coding sequence of clone CW420_2 deposited under accession number ATCC 98292;

(e) a polynucleotide encoding the full-length protein encoded by the cDNA insert of clone CW420_2 deposited under accession number ATCC 98292;

(f) a polynucleotide comprising the nucleotide sequence of the mature protein coding sequence of clone CW420_2 deposited under accession number ATCC 98292;

(g) a polynucleotide encoding the mature protein encoded by the cDNA insert of clone CW420_2 deposited under accession number ATCC 98292;

(h) a polynucleotide encoding a protein comprising the amino acid sequence of SEQ ID NO:10;

(i) a polynucleotide encoding a protein comprising a fragment of the amino acid sequence of SEQ ID NO:10 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:9 from nucleotide 116 to nucleotide 4498; the nucleotide sequence of SEQ ID NO:9 from nucleotide 1221 to nucleotide 1711; the nucleotide sequence of the full-length protein coding sequence of clone CW420_2 deposited under accession number ATCC 98292; or the nucleotide sequence of the mature protein coding sequence of clone CW420_2 deposited under accession number ATCC 98292. In other preferred embodiments, the polynucleotide encodes the full-length or mature protein encoded by the cDNA insert of clone CW420_2 deposited under accession number ATCC 98292. In yet other preferred embodiments, the present invention provides a polynucleotide encoding a protein comprising the amino acid sequence of SEQ ID NO:10 from amino acid 370 to amino acid 532.

Other embodiments provide the gene corresponding to the cDNA sequence of SEQ ID NO:9.

In other embodiments, the present invention provides a composition comprising a protein, wherein said protein comprises an amino acid sequence selected from the group consisting of:

(a) the amino acid sequence of SEQ ID NO:10;

(b) the amino acid sequence of SEQ ID NO:10 from amino acid 370 to amino acid 532;

(c) fragments of the amino acid sequence of SEQ ID NO:10; and (d) the amino acid sequence encoded by the cDNA insert of clone CW420_2 deposited under accession number ATCC 98292;

the protein being substantially free from other mammalian proteins. Preferably such protein comprises the amino acid sequence of SEQ ID NO:10 or the amino acid sequence of SEQ ID NO:10 from amino acid 370 to amino acid 532.

In one embodiment, the present invention provides a composition comprising an isolated polynucleotide selected from the group consisting of:

(a) a polynucleotide comprising the nucleotide sequence of SEQ ID NO:11;

(b) a polynucleotide comprising the nucleotide sequence of SEQ ID NO:11 from nucleotide 119 to nucleotide 2176;

(c) a polynucleotide comprising the nucleotide sequence of SEQ ID NO:11 from nucleotide 1 to nucleotide 529;

(d) a polynucleotide comprising the nucleotide sequence of the full-length protein coding sequence of clone CW795_2 deposited under accession number ATCC 98292;

(e) a polynucleotide encoding the full-length protein encoded by the cDNA insert of clone CW795_2 deposited under accession number ATCC 98292;

(f) a polynucleotide comprising the nucleotide sequence of the mature protein coding sequence of clone CW795_2 deposited under accession number ATCC 98292;

(g) a polynucleotide encoding the mature protein encoded by the cDNA insert of clone CW795_2 deposited under accession number ATCC 98292;

(h) a polynucleotide encoding a protein comprising the amino acid sequence of SEQ ID NO:12;

(i) a polynucleotide encoding a protein comprising a fragment of the amino acid sequence of SEQ ID NO:12 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:11 from nucleotide 119 to nucleotide 2176; the nucleotide sequence of SEQ ID NO:11 from nucleotide 1 to nucleotide 529; the nucleotide sequence of the full-length protein coding sequence of clone CW795_2 deposited under accession number ATCC 98292; or the nucleotide sequence of the mature protein coding sequence of clone CW795_2 deposited under accession number ATCC 98292. In other preferred embodiments, the polynucleotide encodes the full-length or mature protein encoded by the cDNA insert of clone CW795_2 deposited under accession number ATCC 98292. In yet other preferred embodiments, the present invention provides a polynucleotide encoding a protein comprising the amino acid sequence of SEQ ID NO:12 from amino acid 1 to amino acid 137.

Other embodiments provide the gene corresponding to the cDNA sequence of SEQ ID NO:11.

In other embodiments, the present invention provides a composition comprising a protein, wherein said protein comprises an amino acid sequence selected from the group consisting of:

(a) the amino acid sequence of SEQ ID NO:12;

(b) the amino acid sequence of SEQ ID NO:12 from amino acid 1 to amino acid 137;

(c) fragments of the amino acid sequence of SEQ ID NO:12; and (d) the amino acid sequence encoded by the cDNA insert of clone CW795_2 deposited under accession number ATCC 98292;

the protein being substantially free from other mammalian proteins. Preferably such protein comprises the amino acid sequence of SEQ ID NO:12 or the amino acid sequence of SEQ ID NO:12 from amino acid 1 to amino acid 137.

In one embodiment, the present invention provides a composition comprising an isolated polynucleotide selected from the group consisting of:

(a) a polynucleotide comprising the nucleotide sequence of SEQ ID NO:13;

(b) a polynucleotide comprising the nucleotide sequence of SEQ ID NO:13 from nucleotide 401 to nucleotide 589;

(c) a polynucleotide comprising the nucleotide sequence of SEQ ID NO:13 from nucleotide 258 to nucleotide 627;

(d) a polynucleotide comprising the nucleotide sequence of the full-length protein coding sequence of clone CW823_3 deposited under accession number ATCC 98292;

(e) a polynucleotide encoding the full-length protein encoded by the cDNA insert of clone CW823_3 deposited under accession number ATCC 98292;

(f) a polynucleotide comprising the nucleotide sequence of the mature protein coding sequence of clone CW823_3 deposited under accession number ATCC 98292;

(g) a polynucleotide encoding the mature protein encoded by the cDNA insert of clone CW823_3 deposited under accession number ATCC 98292;

(h) a polynucleotide encoding a protein comprising the amino acid sequence of SEQ ID NO:14;

(i) a polynucleotide encoding a protein comprising a fragment of the amino acid sequence of SEQ ID NO:14 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:13 from nucleotide 401 to nucleotide 589; the nucleotide sequence of SEQ ID NO:13 from nucleotide 258 to nucleotide 627; the nucleotide sequence of the full-length protein coding sequence of clone CW823_3 deposited under accession number ATCC 98292; or the nucleotide sequence of the mature protein coding sequence of clone CW823_3 deposited under accession number ATCC 98292. In other preferred embodiments, the polynucleotide encodes the full-length or mature protein encoded by the cDNA insert of clone CW823_3 deposited under accession number ATCC 98292.

Other embodiments provide the gene corresponding to the cDNA sequence of SEQ ID NO:13.

In other embodiments, the present invention provides a composition comprising a protein, wherein said protein comprises an amino acid sequence selected from the group consisting of:

(a) the amino acid sequence of SEQ ID NO:14;

(b) fragments of the amino acid sequence of SEQ ID NO:14; and (c) the amino acid sequence encoded by the cDNA insert of clone CW823_3 deposited under accession number ATCC 98292;

the protein being substantially free from other mammalian proteins. Preferably such protein comprises the amino acid sequence of SEQ ID NO:14.

In one embodiment, the present invention provides a composition comprising an isolated polynucleotide selected from the group consisting of:

(a) a polynucleotide comprising the nucleotide sequence of SEQ ID NO:15;

(b) a polynucleotide comprising the nucleotide sequence of SEQ ID NO:15 from nucleotide 548 to nucleotide 868;

(c) a polynucleotide comprising the nucleotide sequence of SEQ ID NO:15 from nucleotide 590 to nucleotide 868;

(d) a polynucleotide comprising the nucleotide sequence of the full-length protein coding sequence of clone DF989_3 deposited under accession number ATCC 98292;

(e) a polynucleotide encoding the full-length protein encoded by the cDNA insert of clone DF989_3 deposited under accession number ATCC 98292;

(f) a polynucleotide comprising the nucleotide sequence of the mature protein coding sequence of clone DF989_3 deposited under accession number ATCC 98292;

(g) a polynucleotide encoding the mature protein encoded by the cDNA insert of clone DF989_3 deposited under accession number ATCC 98292;

(h) a polynucleotide encoding a protein comprising the amino acid sequence of SEQ ID NO:16;

(i) a polynucleotide encoding a protein comprising a fragment of the amino acid sequence of SEQ ID NO:16 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:15 from nucleotide 548 to nucleotide 868; the nucleotide sequence of SEQ ID NO:15 from nucleotide 590 to nucleotide 868; the nucleotide sequence of the full-length protein coding sequence of clone DF989_3 deposited under accession number ATCC 98292; or the nucleotide sequence of the mature protein coding sequence of clone DF989_3 deposited under accession number ATCC 98292. In other preferred embodiments, the polynucleotide encodes the full-length or mature protein encoded by the cDNA insert of clone DF989_3 deposited under accession number ATCC 98292. In yet other preferred embodiments, the present invention provides a polynucleotide encoding a protein comprising the amino acid sequence of SEQ ID NO:16 from amino acid 75 to amino acid 107.

Other embodiments provide the gene corresponding to the cDNA sequence of SEQ ID NO:15 or SEQ ID NO:17.

In other embodiments, the present invention provides a composition comprising a protein, wherein said protein comprises an amino acid sequence selected from the group consisting of:

(a) the amino acid sequence of SEQ ID NO:16;

(b) the amino acid sequence of SEQ ID NO:16 from amino acid 75 to amino acid 107;

(c) fragments of the amino acid sequence of SEQ ID NO:16; and (d) the amino acid sequence encoded by the cDNA insert of clone DF989_3 deposited under accession number ATCC 98292;

the protein being substantially free from other mammalian proteins. Preferably such protein comprises the amino acid sequence of SEQ ID NO:16 or the amino acid sequence of SEQ ID NO:16 from amino acid 75 to amino acid 107.

In one embodiment, the present invention provides a composition comprising an isolated polynucleotide selected from the group consisting of:

(a) a polynucleotide comprising the nucleotide sequence of SEQ ID NO:18;

(b) a polynucleotide comprising the nucleotide sequence of SEQ ID NO:18 from nucleotide 121 to nucleotide 3345;

(c) a polynucleotide comprising the nucleotide sequence of SEQ ID NO:18 from nucleotide 160 to nucleotide 3345;

(d) a polynucleotide comprising the nucleotide sequence of SEQ ID NO:18 from nucleotide 2592 to nucleotide 3318;

(e) a polynucleotide comprising the nucleotide sequence of the full-length protein coding sequence of clone DL162_2 deposited under accession number ATCC 98292;

(f) a polynucleotide encoding the full-length protein encoded by the cDNA insert of clone DL162_2 deposited under accession number ATCC 98292;

(g) a polynucleotide comprising the nucleotide sequence of the mature protein coding sequence of clone DL162_2 deposited under accession number ATCC 98292;

(h) a polynucleotide encoding the mature protein encoded by the cDNA insert of clone DL162_2 deposited under accession number ATCC 98292;

(i) a polynucleotide encoding a protein comprising the amino acid sequence of SEQ ID NO:19;

(j) a polynucleotide encoding a protein comprising a fragment of the amino acid sequence of SEQ ID NO:19 having biological activity;

(k) a polynucleotide which is an allelic variant of a polynucleotide of (a)–(h) above;

(l) a polynucleotide which encodes a species homologue of the protein of (i) or (j) above; and (m) a polynucleotide capable of hybridizing under stringent conditions to any one of the polynucleotides specified in (a)–(i).

Preferably, such polynucleotide comprises the nucleotide sequence of SEQ ID NO:18 from nucleotide 121 to nucleotide 3345; the nucleotide sequence of SEQ ID NO:18 from nucleotide 160 to nucleotide 3345; the nucleotide sequence of SEQ ID NO:18 from nucleotide 2592 to nucleotide 3318; the nucleotide sequence of the full-length protein coding sequence of clone DL162_2 deposited under accession number ATCC 98292; or the nucleotide sequence of the mature protein coding sequence of clone DL162_2 deposited under accession number ATCC 98292. In other preferred embodiments, the polynucleotide encodes the full-length or mature protein encoded by the cDNA insert of clone DL162_2 deposited under accession number ATCC 98292. In yet other preferred embodiments, the present invention provides a polynucleotide encoding a protein comprising the amino acid sequence of SEQ ID NO:19 from amino acid 860 to amino acid 1066.

Other embodiments provide the gene corresponding to the cDNA sequence of SEQ ID NO:18.

In other embodiments, the present invention provides a composition comprising a protein, wherein said protein comprises an amino acid sequence selected from the group consisting of:

(a) the amino acid sequence of SEQ ID NO:19;

(b) the amino acid sequence of SEQ ID NO:19 from amino acid 860 to amino acid 1066;

(c) fragments of the amino acid sequence of SEQ ID NO:19; and (d) the amino acid sequence encoded by the cDNA insert of clone DL162_2 deposited under accession number ATCC 98292;

the protein being substantially free from other mammalian proteins. Preferably such protein comprises the amino acid sequence of SEQ ID NO:19 or the amino acid sequence of SEQ ID NO:19 from amino acid 860 to amino acid 1066.

In one embodiment, the present invention provides a composition comprising an isolated polynucleotide selected from the group consisting of:

(a) a polynucleotide comprising the nucleotide sequence of SEQ ID NO:32;

(b) a polynucleotide comprising the nucleotide sequence of SEQ ID NO:32 from nucleotide 251 to nucleotide 787;

(c) a polynucleotide comprising the nucleotide sequence of SEQ ID NO:32 from nucleotide 371 to nucleotide 787;

(d) a polynucleotide comprising the nucleotide sequence of the full-length protein coding sequence of clone DL162_1 deposited under accession number ATCC 98292;

(e) a polynucleotide encoding the full-length protein encoded by the cDNA insert of clone DL162_1 deposited under accession number ATCC 98292;

(f) a polynucleotide comprising the nucleotide sequence of the mature protein coding sequence of clone DL162_1 deposited under accession number ATCC 98292;

(g) a polynucleotide encoding the mature protein encoded by the cDNA insert of clone DL162_1 deposited under accession number ATCC 98292;

(h) a polynucleotide encoding a protein comprising the amino acid sequence of SEQ ID NO:33;

(i) a polynucleotide encoding a protein comprising a fragment of the amino acid sequence of SEQ ID NO:33 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:32 from nucleotide 251 to nucleotide 787; the nucleotide sequence of SEQ ID NO:32 from nucleotide 371 to nucleotide 787; the nucleotide sequence of the full-length protein coding sequence of clone DL162_1 deposited under accession number ATCC 98292; or the nucleotide sequence of the mature protein coding sequence of clone DL162_1 deposited under accession number ATCC 98292. In other preferred embodiments, the polynucleotide encodes the full-length or mature protein encoded by the cDNA insert of clone DL162_1 deposited under accession number ATCC 98292. In yet other preferred embodiments, the present invention provides a polynucleotide encoding a protein comprising the amino acid sequence of SEQ ID NO:33 from amino acid 38 to amino acid 170.

Other embodiments provide the gene corresponding to the cDNA sequence of SEQ ID NO:32.

In other embodiments, the present invention provides a composition comprising a protein, wherein said protein comprises an amino acid sequence selected from the group consisting of:

(a) the amino acid sequence of SEQ ID NO:33;

(b) the amino acid sequence of SEQ ID NO:33 from amino acid 38 to amino acid 170;

(c) fragments of the amino acid sequence of SEQ ID NO:33; and (d) the amino acid sequence encoded by the cDNA insert of clone DL162_1 deposited under accession number ATCC 98292;

the protein being substantially free from other mammalian proteins. Preferably such protein comprises the amino acid sequence of SEQ ID NO:33 or the amino acid sequence of SEQ ID NO:33 from amino acid 38 to amino acid 170.

In one embodiment, the present invention provides a composition comprising an isolated polynucleotide selected from the group consisting of:

(a) a polynucleotide comprising the nucleotide sequence of SEQ ID NO:20;

(b) a polynucleotide comprising the nucleotide sequence of SEQ ID NO:20 from nucleotide 117 to nucleotide 2600;

(c) a polynucleotide comprising the nucleotide sequence of SEQ ID NO:20 from nucleotide 2130 to nucleotide 2600;

(d) a polynucleotide comprising the nucleotide sequence of SEQ ID NO:20 from nucleotide 1 to nucleotide 506;

(e) a polynucleotide comprising the nucleotide sequence of the full-length protein coding sequence of clone EC172_1 deposited under accession number ATCC 98292;

(f) a polynucleotide encoding the full-length protein encoded by the cDNA insert of clone EC172_1 deposited under accession number ATCC 98292;

(g) a polynucleotide comprising the nucleotide sequence of the mature protein coding sequence of clone EC172_1 deposited under accession number ATCC 98292;

(h) a polynucleotide encoding the mature protein encoded by the cDNA insert of clone EC172_1 deposited under accession number ATCC 98292;

(i) a polynucleotide encoding a protein comprising the amino acid sequence of SEQ ID NO:21;

(j) a polynucleotide encoding a protein comprising a fragment of the amino acid sequence of SEQ ID NO:21 having biological activity;

(k) a polynucleotide which is an allelic variant of a polynucleotide of (a)–(h) above;

(l) a polynucleotide which encodes a species homologue of the protein of (i) or (j) above; and (m) a polynucleotide capable of hybridizing under stringent conditions to any one of the polynucleotides specified in (a)–(j).

Preferably, such polynucleotide comprises the nucleotide sequence of SEQ ID NO:20 from nucleotide 117 to nucleotide 2600; the nucleotide sequence of SEQ ID NO:20 from nucleotide 2130 to nucleotide 2600; the nucleotide sequence of SEQ ID NO:20 from nucleotide 1 to nucleotide 506; the nucleotide sequence of the full-length protein coding sequence of clone EC172_1 deposited under accession number ATCC 98292; or the nucleotide sequence of the mature protein coding sequence of clone EC172_1 deposited under accession number ATCC 98292. In other preferred embodiments, the polynucleotide encodes the full-length or mature protein encoded by the cDNA insert of clone EC172_1 deposited under accession number ATCC 98292. In yet other preferred embodiments, the present invention provides a polynucleotide encoding a protein comprising the amino acid sequence of SEQ ID NO:21 from amino acid 1 to amino acid 130.

Other embodiments provide the gene corresponding to the cDNA sequence of SEQ ID NO:20.

In other embodiments, the present invention provides a composition comprising a protein, wherein said protein comprises an amino acid sequence selected from the group consisting of:

(a) the amino acid sequence of SEQ ID NO:21;

(b) the amino acid sequence of SEQ ID NO:21 from amino acid 1 to amino acid 130;

(c) fragments of the amino acid sequence of SEQ ID NO:21; and (d) the amino acid sequence encoded by the cDNA insert of clone EC172_1 deposited under accession number ATCC 98292;

the protein being substantially free from other mammalian proteins. Preferably such protein comprises the amino acid sequence of SEQ ID NO:21 or the amino acid sequence of SEQ ID NO:21 from amino acid 1 to amino acid 130.

In certain preferred embodiments, the polynucleotide is operably linked to an expression control sequence. The invention also provides a host cell, including bacterial, yeast, insect and mammalian cells, transformed with such polynucleotide compositions. Also provided by the present invention are organisms that have enhanced, reduced, or modified expression of the gene(s) corresponding to the polynucleotide sequences disclosed herein.

Processes are also provided for producing a protein, which comprise:

(a) growing a culture of the host cell transformed with such polynucleotide compositions in a suitable culture medium; and (b) purifying the protein from the culture.

The protein produced according to such methods is also provided by the present invention. Preferred embodiments include those in which the protein produced by such process is a mature form of the protein.

Protein compositions of the present invention may further comprise a pharmaceutically acceptable carrier. Compositions comprising an antibody which specifically reacts with such protein are also provided by the present invention.

Methods are also provided for preventing, treating or ameliorating a medical condition which comprises administering to a mammalian subject a therapeutically effective amount of a composition comprising a protein of the present invention and a pharmaceutically acceptable carrier.

DETAILED DESCRIPTION

Isolated Proteins and Polynucleotides

Figure 1A:
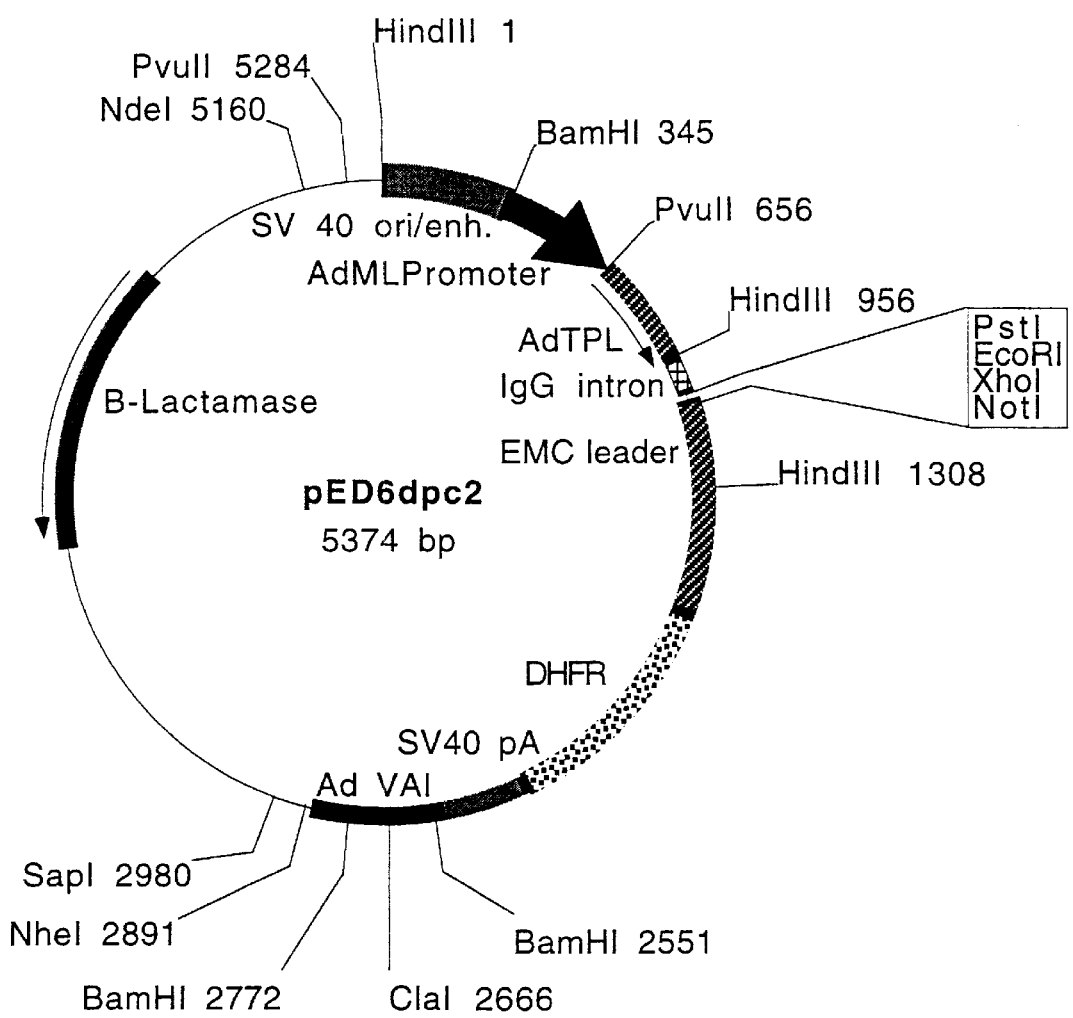
FIGS. 1A and 1B are schematic representations of the pED6 and pNOTs vectors, respectively, used for deposit of clones disclosed herein.

Nucleotide and amino acid sequences, as presently determined, are reported below for each clone and protein disclosed in the present application. The nucleotide sequence of each clone can readily be determined by sequencing of the deposited clone in accordance with known methods. The predicted amino acid sequence (both full-length and mature) can then be determined from such nucleotide sequence. The amino acid sequence of the protein encoded by a particular clone can also be determined by expression of the clone in a suitable host cell, collecting the protein and determining its sequence. For each disclosed protein applicants have identified what they have determined to be the reading frame best identifiable with sequence information available at the time of filing.

As used herein a "secreted" protein is one which, when expressed in a suitable host cell, is transported across or through a membrane, including transport as a result of signal sequences in its amino acid sequence. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum.

Clone "AM666_1"

A polynucleotide of the present invention has been identified as clone "AM666_1". AM666_1 was isolated from a human fetal kidney cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. AM666_1 is a full-length clone, including the entire coding sequence of a secreted protein (also referred to herein as "AM666_1 protein").

The nucleotide sequence of AM666_1 as presently determined is reported in SEQ ID NO:1. What applicants presently believe to be the proper reading frame and the predicted amino acid sequence of the AM666_1 protein corresponding to the foregoing nucleotide sequence is reported in SEQ ID NO:2. Amino acids 15 to 27 are a predicted leader/signal sequence, with the predicted mature amino acid sequence beginning at amino acid 28, or are a transmembrane domain.

The EcoRI/NotI restriction fragment obtainable from the deposit containing clone AM666_1 should be approximately 1300 bp.

The nucleotide sequence disclosed herein for AM666_1 was searched against the GenBank and GeneSeq nucleotide sequence databases using BLASTN/BLASTX and FASTA search protocols. AM666_1 demonstrated at least some similarity with sequences identified as AA493985 (nh07g08.s1 NCI_CGAP_Thy1 *Homo sapiens* cDNA clone). Based upon sequence similarity, AM666_1 proteins and each similar protein or peptide may share at least some activity.

Clone "BN387 3"

A polynucleotide of the present invention has been identified as clone "BN387_3". BN387_3 was isolated from a human adult placenta cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. BN387_3 is a full-length clone, including the entire coding sequence of a secreted protein (also referred to herein as "BN387_3 protein").

The nucleotide sequence of BN387_3 as presently determined is reported in SEQ ID NO:3. What applicants presently believe to be the proper reading frame and the predicted amino acid sequence of the BN387_3 protein corresponding to the foregoing nucleotide sequence is reported in SEQ ID NO:4. Amino acids 14 to 26 are a predicted leader/signal sequence, with the predicted mature amino acid sequence beginning at amino acid 27, or are a transmembrane domain.

The EcoRI/NotI restriction fragment obtainable from the deposit containing clone BN387_3 should be approximately 2000 bp.

The nucleotide sequence disclosed herein for BN387_3 was searched against the GenBank and GeneSeq nucleotide sequence databases using BLASTN/BLASTX and FASTA search protocols. BN387_3 demonstrated at least some similarity with sequences identified as H16912 (ym39d01.r1 *Homo sapiens* cDNA clone 50771 5'). Based upon sequence similarity, BN387_3 proteins and each similar protein or peptide may share at least some activity.

Clone "BO135 2"

A polynucleotide of the present invention has been identified as clone "BQ135_2". BQ135_2 was isolated from a human adult colon (adenocarcinoma Caco2) cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. BQ135_2 is a full-length clone, including the entire coding sequence of a secreted protein (also referred to herein as "BQ135_2 protein").

The nucleotide sequence of BQ135_2 as presently determined is reported in SEQ ID NO:5. What applicants presently believe to be the proper reading frame and the predicted amino acid sequence of the BQ135_2 protein corresponding to the foregoing nucleotide sequence is reported in SEQ ID NO:6.

The EcoRI/NotI restriction fragment obtainable from the deposit containing clone BQ135_2 should be approximately 1200 bp.

The nucleotide sequence disclosed herein for BQ135_2 was searched against the GenBank and GeneSeq nucleotide sequence databases using BLASTN/BLASTX and FASTA search protocols. BQ135_2 demonstrated at least some similarity with sequences identified as AA023751 (mh81f01.r1 Soares mouse placenta 4NbMP13.5 14.5 Mus musculus cDNA clone 457369 5'), AA105433 (ml83g01.r1 Stratagene mouse kidney (#937315) Mus musculus cDNA clone 518640 5'), D64061 (Rat brain mRNA for annexin V-binding protein (ABP-7), partial cds), and N67257 (yz49b08.s1 *Homo sapiens* cDNA clone 286359 3'). The predicted amino acid sequence disclosed herein for BQ135_2 was searched against the GenPept and GeneSeq amino acid sequence databases using the BLASTX search protocol. The predicted BQ135_2 protein demonstrated at least some similarity to sequences identified as D64061 (annexin V-binding protein (ABP-7) [Rattus norvegicus]). Annexins associate with membranes and act as ion channels, they can also act as an autocrine factor that enhances osteoclast formation and bone resorption. Annexins have been localized in nucleoli and mitochondria but also in the cytoplasm, plasma (i.e. blood) and in association with vesicles. They are probably involved in fusing vesicles to each other and to plasma membranes causing secretion of vesicular contents. Specifically they have a calcium-dependent ability to bind phospholipids. Thus they are membrane associated. It is possible that annexin-binding proteins are also membrane associated even though they are highly hydrophilic through the same mechanism (electrostatic interaction with phospholipids of membranes). Based upon sequence similarity, BQ135_2 proteins and each similar protein or peptide may share at least some activity.

Clone "CR678_1"

A polynucleotide of the present invention has been identified as clone "CR678_1". CR678_1 was isolated from a human adult testes cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. CR678_1 is a full-length clone, including the entire coding sequence of a secreted protein (also referred to herein as "CR678_1 protein").

The nucleotide sequence of CR678_1 as presently determined is reported in SEQ ID NO:7. What applicants presently believe to be the proper reading frame and the predicted amino acid sequence of the CR678_1 protein corresponding to the foregoing nucleotide sequence is reported in SEQ ID NO:8.

The EcoRI/NotI restriction fragment obtainable from the deposit containing clone CR678_1 should be approximately 870 bp.

The nucleotide sequence disclosed herein for CR678_1 was searched against the GenBank and GeneSeq nucleotide sequence databases using BLASTN/BLASTX and FASTA search protocols. CR678_1 demonstrated at least some similarity with sequences identified as X85232 (*H.sapiens* chromosome 3 sequences). Based upon sequence similarity, CR678_1 proteins and each similar protein or peptide may share at least some activity. The nucleotide sequence of CR678_1 indicates that it may contain an Alu repetitive element.

Clone "CW420_2"

A polynucleotide of the present invention has been identified as clone "CW420_2". CW420_2 was isolated from a human fetal brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. CW420_2 is a full-length clone, including the entire coding sequence of a secreted protein (also referred to herein as "CW420_2 protein").

The nucleotide sequence of CW420_2 as presently determined is reported in SEQ ID NO:9. What applicants presently believe to be the proper reading frame and the predicted amino acid sequence of the CW420_2 protein corresponding to the foregoing nucleotide sequence is reported in SEQ ID NO:10.

The EcoRI/NotI restriction fragment obtainable from the deposit containing clone CW420_2 should be approximately 5100 bp.

The nucleotide sequence disclosed herein for CW420_2 was searched against the GenBank and GeneSeq nucleotide sequence databases using BLASTN/BLASTX and FASTA search protocols. CW420_2 demonstrated at least some similarity with sequences identified as T55440 (yb38e09.s1 *Homo sapiens* cDNA clone 73480 3'). Based upon sequence similarity, CW420_2 proteins and each similar protein or peptide may share at least some activity. The TopPredII computer program predicts two potential transmembrane domains within the CW420_2 protein sequence centered around amino acids 500 and 1270 of SEQ ID NO:10.

Clone "CW795_2"

A polynucleotide of the present invention has been identified as clone "CW795_2". CW795_2 was isolated from a human fetal brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. CW795_2 is a full-length clone, including the entire coding sequence of a secreted protein (also referred to herein as "CW795_2 protein").

The nucleotide sequence of CW795_2 as presently determined is reported in SEQ ID NO:11. What applicants presently believe to be the proper reading frame and the predicted amino acid sequence of the CW795_2 protein corresponding to the foregoing nucleotide sequence is reported in SEQ ID NO:12.

The EcoRI/NotI restriction fragment obtainable from the deposit containing clone CW795_2 should be approximately 3000 bp.

The nucleotide sequence disclosed herein for CW795_2 was searched against the GenBank and GeneSeq nucleotide sequence databases using BLASTN/BLASTX and FASTA search protocols. CW795_2 demonstrated at least some similarity with sequences identified as AA115676 (zl86a09.s1 Stratagene colon (#937204) *Homo sapiens* cDNA clone 511480 3'), N22955 (yw44h07.s1 *Homo sapiens* cDNA clone 255133 3'), and W56804 (zd16g06.s1 Soares fetal heart NbHH19W *Homo sapiens* cDNA clone 340858 3'). The predicted amino acid sequence disclosed herein for CW795_2 was searched against the GenPept, GeneSeq, and SwissProt amino acid sequence databases using the BLASTX search protocol. The predicted CW795_2 protein demonstrated at least some similarity to sequences identified as X81068 (probable mitochondrial protein) and the yeast proteins rcal and afg3 (tat-binding homologues). Based upon sequence similarity, CW795_2 proteins and each similar protein or peptide may share at least some activity. The TopPredII computer program predicts two potential transmembrane domains within the CW795_2 protein sequence centered around amino acids 60 and 170 of SEQ ID NO:12.

Clone "CW823_3"

A polynucleotide of the present invention has been identified as clone "CW823_3". CW823_3 was isolated from a human fetal brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. CW823_3 is a full-length clone, including the entire coding sequence of a secreted protein (also referred to herein as "CW823_3 protein").

The nucleotide sequence of CW823_3 as presently determined is reported in SEQ ID NO:13. What applicants presently believe to be the proper reading frame and the predicted amino acid sequence of the CW823_3 protein corresponding to the foregoing nucleotide sequence is reported in SEQ ID NO:14.

The EcoRI/NotI restriction fragment obtainable from the deposit containing clone CW823_3 should be approximately 600 bp.

The nucleotide sequence disclosed herein for CW823_3 was searched against the GenBank and GeneSeq nucleotide sequence databases using BLASTN/BLASTX and FASTA search protocols. No hits were found in the database.

Clone "DF989_3"

A polynucleotide of the present invention has been identified as clone "DF989_3". DF989_3 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. DF989_3 is a full-length clone, including the entire coding sequence of a secreted protein (also referred to herein as "DF989_3 protein").

The nucleotide sequence of the 5' portion of DF989_3 as presently determined is reported in SEQ ID NO:15. What applicants presently believe is the proper reading frame for the coding region is indicated in SEQ ID NO:16. The predicted amino acid sequence of the DF989_3 protein corresponding to the foregoing nucleotide sequence is reported in SEQ ID NO:16. Amino acids 2 to 14 are a predicted leader/signal sequence, with the predicted mature amino acid sequence beginning at amino acid 15, or are a transmembrane domain. Additional nucleotide sequence from the 3' portion of DF989_3, including the polyA tail, is reported in SEQ ID NO:17.

The EcoRI/NotI restriction fragment obtainable from the deposit containing clone DF989_3 should be approximately 1800 bp.

The nucleotide sequence disclosed herein for DF989_3 was searched against the GenBank and GeneSeq nucleotide sequence databases using BLASTN/BLASTX and FASTA search protocols. DF989_3 demonstrated at least some similarity with sequences identified as R24724 (yg43c05.r1 *Homo sapiens* cDNA clone 35337 5') and T33717 (EST58870 *Homo sapiens* cDNA 5' end similar to None). Based upon sequence similarity, DF989_3 proteins and each similar protein or peptide may share at least some activity.

Clone "DL162_2"

A polynucleotide of the present invention has been identified as clone "DL162_2". DL162_2 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. DL162_2 is a full-length clone, including the entire coding sequence of a secreted protein (also referred to herein as "DL162_2 protein").

The nucleotide sequence of DL162_2 as presently determined is reported in SEQ ID NO:18. What applicants presently believe to be the proper reading frame and the predicted amino acid sequence of the DL162_2 protein corresponding to the foregoing nucleotide sequence is reported in SEQ ID NO:19. Amino acids 1 to 13 are a predicted leader/signal sequence, with the predicted mature amino acid sequence beginning at amino acid 14, or are a transmembrane domain.

The EcoRI/NotI restriction fragment obtainable from the deposit containing clone DL162_2 should be approximately 4000 bp.

The predicted amino acid sequence disclosed herein for DL162_2 was searched against the GenPept and GeneSeq amino acid sequence databases using the BLASTX search protocol. The predicted DL162_2 protein demonstrated at least some similarity to sequences identified as GenPept 2224563 (KIAA protein [*Homo sapiens*]). The TopPredII computer program predicts a potential transmembrane domains within the DL162_2 protein sequence near the carboxyl terminus of SEQ ID NO:19.

Clone "DL162_1"

A polynucleotide of the present invention has been identified as clone "DL162_1". DL162_1 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. DL162_1 is a full-length clone, including the entire coding sequence of a secreted protein (also referred to herein as "DL162_1 protein").

The nucleotide sequence of DL162_1 as presently determined is reported in SEQ ID NO:32. What applicants presently believe to be the proper reading frame and the predicted amino acid sequence of the DL162_1 protein corresponding to the foregoing nucleotide sequence is reported in SEQ ID NO:33. Amino acids 28 to 40 are a predicted leader/signal sequence, with the predicted mature amino acid sequence beginning at amino acid 41, or are a transmembrane domain.

The nucleotide sequence disclosed herein for DL162_1 was searched against the GenBank and GeneSeq nucleotide sequence databases using BLASTN/BLASTX and FASTA search protocols. No hits were found in the database.

Clone "EC172_1"

A polynucleotide of the present invention has been identified as clone "EC172_1". EC172_1 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. EC172_1 is a full-length clone, including the entire coding sequence of a secreted protein (also referred to herein as "EC172_1 protein").

The nucleotide sequence of EC172_1 as presently determined is reported in SEQ ID NO:20. What applicants presently believe to be the proper reading frame and the predicted amino acid sequence of the EC172_1 protein corresponding to the foregoing nucleotide sequence is reported in SEQ ID NO:21. Amino acids 659 to 671 are a predicted leader/signal sequence, with the predicted mature amino acid sequence beginning at amino acid 672, or are a transmembrane domain.

The EcoRI/NotI restriction fragment obtainable from the deposit containing clone EC172_1 should be approximately 4000 bp.

The nucleotide sequence disclosed herein for EC172_1 was searched against the GenBank and GeneSeq nucleotide sequence databases using BLASTN/BLASTX and FASTA search protocols. EC172_1 demonstrated at least some similarity with sequences identified as H31192 (EST104991 Rattus sp. cDNA 3' end similar to *C.elegans* hypothetical protein ZK1098.10) and U29585 (*Streptococcus pyogenes* emm18.1). The predicted amino acid sequence disclosed herein for EC172_1 was searched against the GenPept and GeneSeq amino acid sequence databases using the BLASTX search protocol. The predicted EC172_1 protein demonstrated at least some similarity to sequences identified as Z22176 (ZK1098.10 [*Caenorhabditis elegans*]). Based upon sequence similarity, EC172_1 proteins and each similar protein or peptide may share at least some activity.

Deposit of Clones

Clones AM666_1, BN387_3, BQ135_2, CR678_1, CW420_2, CW795_2, CW823_3, DF989_3, DL162_2, DL162_1, and EC172_1 were deposited on Jan. 10, 1997 with the American Type Culture Collection 10801 University Boulevard, Maanassas, Va., 20110-2209, U.S.A., as an original deposit under the Budapest Treaty and were given the accession number ATCC 98292, from which each clone comprising a particular polynucleotide is obtainable. All restrictions on the availability to the public of the deposited material will be irrevocably removed upon the granting of the patent, except for the requirements specified in 37 C.F.R. § 1.808(b).

Figure 1B:
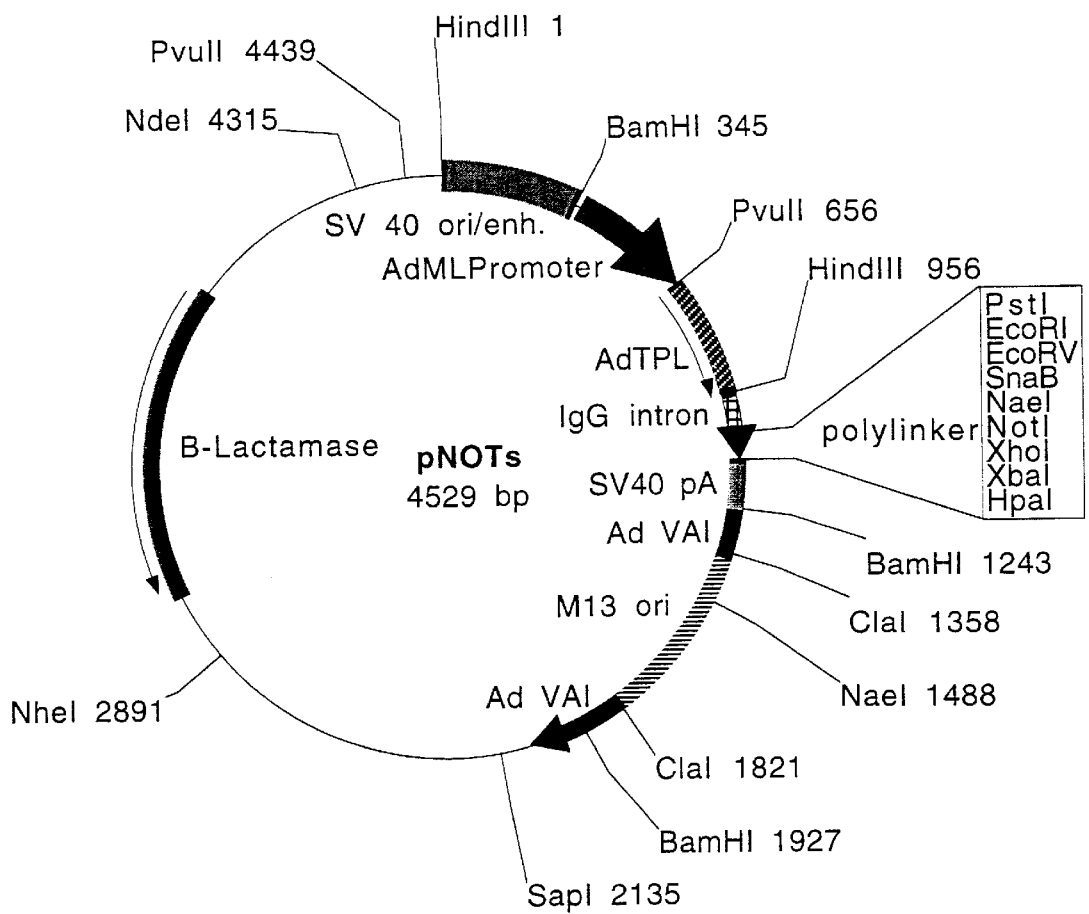

Each clone has been transfected into separate bacterial cells (*E. coli*) in this composite deposit. Each clone can be removed from the vector in which it was deposited by performing an EcoRI/NotI digestion (5' site, EcoRI; 3' site, NotI) to produce the appropriate fragment for such clone. Each clone was deposited in either the pED6 or pNOTs vector depicted in FIG. 1. The pED6dpc2 vector ("pED6") was derived from pED6dpc1 by insertion of a new polylinker to facilitate cDNA cloning (Kaufman et al., 1991, *Nucleic Acids Res.* 19: 4485–4490); the pNOTs vector was derived from pMT2 (Kaufman et al., 1989, *Mol. Cell. Biol.* 9: 946–958) by deletion of the DHFR sequences, insertion of a new polylinker, and insertion of the M13 origin of replication in the ClaI site. In some instances, the deposited clone can become "flipped" (i.e., in the reverse orientation) in the deposited isolate. In such instances, the cDNA insert can still be isolated by digestion with EcoRI and NotI. However, NotI will then produce the 5' site and EcoRI will produce the 3' site for placement of the cDNA in proper orientation for expression in a suitable vector. The cDNA may also be expressed from the vectors in which they were deposited.

Bacterial cells containing a particular clone can be obtained from the composite deposit as follows:

An oligonucleotide probe or probes should be designed to the sequence that is known for that particular clone. This sequence can be derived from the sequences provided herein, or from a combination of those sequences. The sequence of the oligonucleotide probe that was used to isolate each full-length clone is identified below, and should be most reliable in isolating the clone of interest.

| Clone | Probe Sequence |
| --- | --- |
| AM666_1 | SEQ ID NO:22 |
| BN387_3 | SEQ ID NO:23 |
| BQ135_2 | SEQ ID NO:24 |
| CR678_1 | SEQ ID NO:25 |
| CW420_2 | SEQ ID NO:26 |
| CW795_2 | SEQ ID NO:27 |
| CW823_3 | SEQ ID NO:28 |
| DF989_3 | SEQ ID NO:29 |

-continued

| Clone | Probe Sequence |
| --- | --- |
| DL162_2, DL162_1 | SEQ ID NO:30 |
| EC172_1 | SEQ ID NO:31 |

In the sequences listed above which include an N at position 2, that position is occupied in preferred probes/primers by a biotinylated phosphoaramidite residue rather than a nucleotide (such as, for example, that produced by use of biotin phosphoramidite (1-dimethoxytrityloxy-2-(N-biotinyl-4-aminobutyl)-propyl-3-O-(2-cyanoethyl)-(N,N-diisopropyl)-phosphoramadite) (Glen Research, cat. no. 10-1953)).

The design of the oligonucleotide probe should preferably follow these parameters:

(a) It should be designed to an area of the sequence which has the fewest ambiguous bases ("N's"), if any;

(b) It should be designed to have a $T_m$ of approx. 80° C. (assuming 2° for each A or T and 4 degrees for each G or C). The oligonucleotide should preferably be labeled with g-$^{32}$P ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately 4e+6 dpm/pmole.

The bacterial culture containing the pool of full-length clones should preferably be thawed and 100 μl of the stock used to inoculate a sterile culture flask containing 25 ml of sterile L-broth containing ampicillin at 100 μg/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 μg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them.

The filter is then preferably incubated at 65° C. for 1 hour with gentle agitation in 6×SSC (20×stock is 175.3 g NaCl/liter, 88.2 g Na citrate/liter, adjusted to pH 7.0 with NaOH) containing 0.5% SDS, 100 μg/ml of yeast RNA, and 10 mM EDTA (approximately 10 mL per 150 mm filter). Preferably, the probe is then added to the hybridization mix at a concentration greater than or equal to 1e+6 dpm/mL. The filter is then preferably incubated at 65° C. with gentle agitation overnight. The filter is then preferably washed in 500 mL of 2×SSC/0.5% SDS at room temperature without agitation, preferably followed by 500 mL of 2×SSC/0.1% SDS at room temperature with gentle shaking for 15 minutes. A third wash with 0.1×SSC/0.5% SDS at 65° C. for 30 minutes to 1 hour is optional. The filter is then preferably dried and subjected to autoradiography for sufficient time to visualize the positives on the X-ray film. Other known hybridization methods can also be employed.

The positive colonies are picked, grown in culture, and plasmid DNA isolated using standard procedures. The clones can then be verified by restriction analysis, hybridization analysis, or DNA sequencing.

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al., J. Amer. Chem. Soc. 114 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein—IgM fusion would generate a decavalent form of the protein of the invention.

The present invention also provides both full-length and mature forms of the disclosed proteins. The full-length form of the such proteins is identified in the sequence listing by translation of the nucleotide sequence of each disclosed clone. The mature form of such protein may be obtained by expression of the disclosed full-length polynucleotide (preferably those deposited with ATCC) in a suitable mammalian cell or other host cell. The sequence of the mature form of the protein may also be determinable from the amino acid sequence of the full-length form.

The present invention also provides genes corresponding to the polynucleotide sequences disclosed herein. "Corresponding genes" are the regions of the genome that are transcribed to produce the mRNAs from which cDNA polynucleotide sequences are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" is a gene that has been separated from the adjacent coding sequences, if any, present in the genome of the organism from which the gene was isolated.

Organisms that have enhanced, reduced, or modified expression of the gene(s) corresponding to the polynucleotide sequences disclosed herein are provided. The desired change in gene expression can be achieved through the use of antisense polynucleotides or ribozymes that bind and/or cleave the mRNA transcribed from the gene (Albert and Morris, 1994, Trends Pharmacol. Sci. 15(7): 250–254; Lavarosky et al., 1997, Biochem. Mol. Med. 62(1): 11–22; and Hampel, 1998, Prog. Nucleic Acid Res. Mol. Biol. 58: 1–39; all of which are incorporated by reference herein). Transgenic animals that have multiple copies of the gene(s) corresponding to the polynucleotide sequences disclosed herein, preferably produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see European Patent No. 0 649 464 B1, incorporated by reference herein). In addition, organisms are provided in which the gene(s) corresponding to the polynucleotide sequences disclosed herein have been partially or completely inactivated, through insertion of extraneous sequences into the corresponding gene(s) or through deletion of all or part of the corresponding gene(s). Partial or complete gene inactivation can be accomplished through insertion, preferably followed by imprecise excision, of transposable elements (Plasterk, 1992, Bioessays 14(9): 629–633; Zwaal et al., 1993, Proc. Natl. Acad. Sci. USA 90(16): 7431–7435; Clark et al., 1994, Proc. Natl. Acad. Sci. USA 91(2): 719–722; all of which are incorporated by reference herein), or through homologous recombination, preferably detected by positive/negative genetic selection strategies (Mansour et al., 1988, Nature 336: 348–352; U.S. Pat. Nos. 5,464,764; 5,487,992; 5,627,059; 5,631,153; 5,614,396; 5,616,491; and 5,679,523; all of which are incorporated by reference herein). These organisms with altered gene expression are preferably eukaryotes and more preferably are mammals. Such organisms are useful for the development of non-human models for the study of disorders involving the corresponding gene(s), and for the development of assay systems for the identification of molecules that interact with the protein product(s) of the corresponding gene(s).

Where the protein of the present invention is membrane-bound (e.g., is a receptor), the present invention also provides for soluble forms of such protein. In such forms part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information.

Proteins and protein fragments of the present invention include proteins with amino acid sequence lengths that are at least 25% (more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

Species homologs of the disclosed polynucleotides and proteins are also provided by the present invention. As used herein, a "species homologue" is a protein or polynucleotide with a different species of origin from that of a given protein or polynucleotide, but with significant sequence similarity to the given protein or polynucleotide, as determined by those of skill in the art. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous, or related to that encoded by the polynucleotides.

The invention also includes polynucleotides with sequences complementary to those of the polynucleotides disclosed herein.

The present invention also includes polynucleotides capable of hybridizing under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A–F; stringent conditions are at least as stringent as, for example, conditions G–L; and reduced stringency conditions are at least as stringent as, for example, conditions M–R.

identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≥50 | 65° C.; 1xSSC -or- 42° C.; 1xSSC, 500% formamide | 65° C.; 0.3xSSC |
| B | DNA:DNA | <50 | $T_B^*$; 1xSSC | $T_B^*$; 1xSSC |
| C | DNA:RNA | ≥50 | 67° C.; 1xSSC -or- 45° C.; 1xSSC, 50% formamide | 67° C.; 0.3xSSC |
| D | DNA:RNA | <50 | $T_D^*$; 1xSSC | $T_D^*$; 1xSSC |
| E | RNA:RNA | ≥50 | 70° C.; 1xSSC -or- 50° C.; 1xSSC, 50% formamide | 70° C.; 0.3xSSC |
| F | RNA:RNA | <50 | $T_F^*$; 1xSSC | $T_F^*$; 1xSSC |
| G | DNA:DNA | ≥50 | 65° C.; 4xSSC -or- 42° C.; 4xSSC, 50% formamide | 65° C.; 1xSSC |
| H | DNA:DNA | <50 | $T_H^*$; 4xSSC | $T_H^*$; 4xSSC |
| I | DNA:RNA | ≥50 | 67° C.; 4xSSC -or- 45° C.; 4xSSC, 50% formamide | 67° C.; 1xSSC |
| J | DNA:RNA | <50 | $T_J^*$; 4xSSC | $T_J^*$; 4xSSC |
| K | RNA:RNA | ≥50 | 70° C.; 4xSSC -or- 50° C.; 4xSSC, 50% formamide | 67° C.; 1xSSC |
| L | RNA:RNA | <50 | $T_L^*$; 2xSSC | $T_L^*$; 2xSSC |
| M | DNA:DNA | ≥50 | 50° C.; 4xSSC -or- 40° C.; 6xSSC, 50% formamide | 50° C.; 2xSSC |
| N | DNA:DNA | <50 | $T_N^*$; 6xSSC | $T_N^*$; 6xSSC |
| O | DNA:RNA | ≥50 | 55° C.; 4xSSC -or- 42° C.; 6xSSC, 50% formamide | 55° C.; 2xSSC |
| P | DNA:RNA | <50 | $T_P^*$; 6xSSC | $T_P^*$; 6xSSC |
| Q | RNA:RNA | ≥50 | 60° C.; 4xSSC -or- 45° C.; 6xSSC, 50% formamide | 60° C.; 2xSSC |
| R | RNA:RNA | <50 | $T_R^*$; 4xSSC | $T_R^*$; 4xSSC |

‡: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
†: SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.
*$T_B$–$T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}$[$Na^+$]) + 0.41(% G + C) − (600/N), where N is the number of bases in the hybrid, and [$Na^+$] is the concentration of sodium ions in the hybridization buffer ([$Na^+$] for 1xSSC = 0.165M).

Additional examples of stringency conditions for polynucleotide hybridization are provided in Sambrook, J., E. F. Fritsch, and T. Maniatis, 1989, *Molecular Cloning: A Laboratory Manual,* Cold Spring Harbor Laboratory Press, Cold Spring Harbor, N.Y., chapters 9 and 11, and *Current Protocols in Molecular Biology,* 1995, F. M. Ausubel et al., eds., John Wiley & Sons, Inc., sections 2.10 and 6.3–6.4, incorporated herein by reference.

Preferably, each such hybridizing polynucleotide has a length that is at least 25%(more preferably at least 50%, and most preferably at least 75%) of the length of the polynucleotide of the present invention to which it hybridizes, and has at least 60% sequence identity (more preferably, at least 75% are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No. 1555* (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

Uses and Biological Activity

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152: 1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In *Current Protocols in Immunology*. J. E. e. a. Coligan eds. Vol 1 pp. 3.12.1–3.12.14, John Wiley and Sons, Toronto. 1994; and Measurement of mouse and human Interferon γ, Schreiber, R. D. In *Current Protocols in Immunology*. J. E. e. a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In *Current Protocols in Immunology*. J. E. e. a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6-Nordan, R. In *Current Protocols in Immunology*. J. E. e. a. Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11-Bennett, F., Giannotti, J., Clark, S. C. and Turner, K. J. In *Current Protocols in Immunology*. J. E. e. a. Coligan eds. Vol 1 pp. 6.15.1 John Wiley and Sons, Toronto. 1991; Measurement of mouse and human Interleukin 9-Ciarletta, A., Giannotti, J., Clark, S. C. and Turner, K. J. In *Current Protocols in Immunology*. J. E. e. a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Immune Stimulating or Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as , for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I α chain protein and $\beta_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E. e. a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640,1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney, M. G. In *Culture of Hematopoietic Cells*. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. *In Culture of Hematopoietic Cells*. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In *Culture of Hematopoietic Cells*. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In *Culture of Hematopoietic Cells*. R. I. Freshney, et al. eds. Vol pp. 163–179, Wiley-Liss, Inc., New York, N.Y. 1994; Long term culture initiating cell assay, Sutherland, H. J. In *Culture of Hematopoietic Cells*. R. I. Freshney, et al. eds. Vol pp. 139–162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, *Epidermal Wound Healing*, pps. 71–112 (Maibach, H I and Rovee, D T, eds.), Year Book Medical Publishers, Inc., Chicago, as modified by Eaglstein and Mertz, J. Invest. Dermatol 71:382–84 (1978).

Activin/Inhibin Activity

A protein of the present invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin α family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W.Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25: 1744–1748; Gruber et al. J. of Immunol. 152:5860–5867, 1994; Johnston et al. J. of Immunol. 153: 1762–1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419,1987; Humphrey et al., Fibrinolysis 5:71–79 (1991); Schaub, Prostaglandins 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in:Current Protocols in Immunology, Ed by J. E. Coligan, A. M. Kruisbeek, D. H. Margulies, E. M. Shevach, W.Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Cadherin/Tumor Invasion Suppressor Activity

Cadherins are calcium-dependent adhesion molecules that appear to play major roles during development, particularly in defining specific cell types. Loss or alteration of normal cadherin expression can lead to changes in cell adhesion properties linked to tumor growth and metastasis. Cadherin malfunction is also implicated in other human diseases, such as pemphigus vulgaris and pemphigus foliaceus (autoimmune blistering skin diseases), Crohn's disease, and some developmental abnormalities.

The cadherin superfamily includes well over forty members, each with a distinct pattern of expression. All members of the superfamily have in common conserved extracellular repeats (cadherin domains), but structural differences are found in other parts of the molecule. The cadherin domains bind calcium to form their tertiary structure and thus calcium is required to mediate their adhesion. Only a few amino acids in the first cadherin domain provide the basis for homophilic adhesion; modification of this recognition site can change the specificity of a cadherin so that instead of recognizing only itself, the mutant molecule can now also bind to a different cadherin. In addition, some cadherins engage in heterophilic adhesion with other cadherins.

E-cadherin, one member of the cadherin superfamily, is expressed in epithelial cell types. Pathologically, if E-cadherin expression is lost in a tumor, the malignant cells become invasive and the cancer metastasizes. Transfection of cancer cell lines with polynucleotides expressing E-cadherin has reversed cancer-associated changes by returning altered cell shapes to normal, restoring cells' adhesiveness to each other and to their substrate, decreasing the cell growth rate, and drastically reducing anchorage-independent cell growth. Thus, reintroducing E-cadherin expression reverts carcinomas to a less advanced stage. It is likely that other cadherins have the same invasion suppressor role in carcinomas derived from other tissue types. Therefore, proteins of the present invention with cadherin activity, and polynucleotides of the present invention encoding such proteins, can be used to treat cancer. Introducing such proteins or polynucleotides into cancer cells can reduce or eliminate the cancerous changes observed in these cells by providing normal cadherin expression.

Cancer cells have also been shown to express cadherins of a different tissue type than their origin, thus allowing these cells to invade and metastasize in a different tissue in the body. Proteins of the present invention with cadherin activity, and polynucleotides of the present invention encoding such proteins, can be substituted in these cells for the inappropriately expressed cadherins, restoring normal cell adhesive properties and reducing or eliminating the tendency of the cells to metastasize.

Additionally, proteins of the present invention with cadherin activity, and polynucleotides of the present invention encoding such proteins, can used to generate antibodies recognizing and binding to cadherins. Such antibodies can be used to block the adhesion of inappropriately expressed tumor-cell cadherins, preventing the cells from forming a tumor elsewhere. Such an anti-cadherin antibody can also be used as a marker for the grade, pathological type, and prognosis of a cancer, i.e. the more progressed the cancer, the less cadherin expression there will be, and this decrease in cadherin expression can be detected by the use of a cadherin-binding antibody.

Fragments of proteins of the present invention with cadherin activity, preferably a polypeptide comprising a decapeptide of the cadherin recognition site, and polynucleotides of the present invention encoding such protein fragments, can also be used to block cadherin function by binding to cadherins and preventing them from binding in ways that produce undesirable effects. Additionally, fragments of proteins of the present invention with cadherin activity, preferably truncated soluble cadherin fragments which have been found to be stable in the circulation of cancer patients, and polynucleotides encoding such protein fragments, can be used to disturb proper cell-cell adhesion.

Assays for cadherin adhesive and invasive suppressor activity include, without limitation, those described in: Hortsch et al. J Biol Chem 270 (32): 18809–18817, 1995; Miyaki et al. Oncogene 11: 2547–2552, 1995; Ozawa et al. Cell 63:1033–1038, 1990.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

Administration and Dosing

A protein of the present invention (from whatever source derived, including without limitation from recombinant and non-recombinant sources) may be used in a pharmaceutical composition when combined with a pharmaceutically acceptable carrier. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A protein of the present invention may be active in multimers (e.g., heterodimers or homodimers) or complexes with itself or other proteins. As a result, pharmaceutical compositions of the invention may comprise a protein of the invention in such multimeric or complexed form.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunolgobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 ng to about 10 mg, more preferably about 0.1 $\mu$g to about 1 mg) of protein of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer.Chem.Soc. 85, 2149–2154 (1963); J. L. Krstenansky, et al., FEBS Lett. 211 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells.

In further compositions, proteins of the invention may be combined with other agents beneficial to the treatment of the bone and/or cartilage defect, wound, or tissue in question.

These agents include various growth factors such as epidermal growth factor (EGF), platelet derived growth factor (PDGF), transforming growth factors (TGF-$\alpha$ and TGF-$\beta$), and insulin-like growth factor (IGF).

The therapeutic compositions are also presently valuable for veterinary applications. Particularly domestic animals and thoroughbred horses, in addition to humans, are desired patients for such treatment with proteins of the present invention.

The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of proteins of the present invention in order to proliferate or to produce a desired effect on or activity in such cells. Treated cells can then be introduced in vivo for therapeutic purposes.

Patent and literature references cited herein are incorporated by reference as if fully set forth.

What is claimed is:

1. An isolated polynucleotide selected from the group consisting of:
   (a) a polynucleotide comprising the nucleotide sequence of SEQ ID NO:1;
   (b) a polynucleotide comprising the nucleotide sequence of SEQ ID NO:1 from nucleotide 918 to nucleotide 1262;
   (c) a polynucleotide comprising the nucleotide sequence of SEQ ID NO:1 from nucleotide 999 to nucleotide 1262;
   (d) a polynucleotide comprising the nucleotide sequence of SEQ ID NO:1 from nucleotide 928 to nucleotide 1134;
   (e) a polynucleotide comprising the nucleotide sequence of the full-length protein coding sequence of clone AM666_1 deposited under accession number ATCC 98292;
   (f) a polynucleotide encoding the full-length protein encoded by the cDNA insert of clone AM666_1 deposited under accession number ATCC 98292;
   (g) a polynucleotide comprising the nucleotide sequence of the mature protein coding sequence of done AM666_1 deposited under accession number ATCC 98292;
   (h) a polynucleotide encoding the mature protein encoded by the cDNA insert of clone AM666_1 deposited under accession number ATCC 98292;
   (i) a polynucleotide encoding a protein comprising the amino acid sequence of SEQ ID NO:2;
   (j) a polynucleotide encoding a protein comprising a fragment of the amino acid sequence of SEQ ID NO:2, the fragment comprising the amino acid sequence of SEQ ID NO:2 from amino acid 5 to amino acid 72;
   (k) a polynucleotide encoding a protein comprising a fragment of the amino acid sequence of SEQ ID NO:2, the fragment comprising the amino acid sequence of SEQ ID NO:2 from amino acid 28 to amino acid 115; and
   (l) a polynucleotide that hybridizes in 6×SSC at 65 degrees C. to any one of the polynucleotides specified in (a)–(k) and that has a length that is at least 25% of the length of SEQ ID NO:1.

2. The polynucleotide of claim 1 wherein said polynucleotide is operably linked to at least one expression control sequence.

3. A host cell transformed with the polynucleotide of claim 2.

4. The host cell of claim 3, wherein said cell is a mammalian cell.

5. A process for producing a protein encoded by the polynucleotide of claim 2, which process comprises:
   (a) growing a culture of the host cell of claim 3 in a suitable culture medium; and
   (b) purifying said protein from the culture.

6. An isolated polynucleotide encoding a protein, wherein the protein is produced according to the process of claim 5.

7. The polynucleotide of claim 6, wherein the polynucleotide comprises the cDNA insert of clone AM666_1 deposited under accession number ATCC 98292.

8. The polynucleotide of claim 1, wherein the polynucleotide comprises the nucleotide sequence of SEQ ID NO:1.

9. The polynucleotide of claim 1, wherein the polynucleotide comprises the nucleotide sequence of SEQ ID NO:1 from nucleotide 918 to nucleotide 1262.

10. The polynucleotide of claim 1, wherein the polynucleotide comprises the nucleotide sequence of SEQ ID NO:1 from nucleotide 999 to nucleotide 1262.

11. The polynucleotide of claim 1, wherein the polynucleotide comprises the nucleotide sequence of SEQ ID NO:1 from nucleotide 928 to nucleotide 1134.

12. The polynucleotide of claim 1, wherein the polynucleotide comprises the nucleotide sequence of the full-length protein coding sequence of clone AM666_1 deposited under accession number ATCC 98292.

13. The polynucleotide of claim 1, wherein the polynucleotide encodes the full-length protein encoded by the cDNA insert of clone AM666_1 deposited under accession number ATCC 98292.

14. The polynucleotide of claim 1, wherein the polynucleotide comprises the nucleotide sequence of the mature protein coding sequence of AM666_1 deposited under accession number ATCC 98292.

15. The polynucleotide of claim 1, wherein the polynucleotide encodes the mature protein encoded by the cDNA insert of clone AM666_1 deposited under accession number ATCC 98292.

16. The polynucleotide of claim 1, wherein the polynucleotide encodes a protein comprising the amino acid sequence of SEQ ID NO:2.

17. The polynucleotide of claim 1, wherein the polynucleotide encodes a protein comprising a fragment of the amino acid sequence of SEQ ID NO:2, the fragment comprising the amino acid sequence of SEQ ID NO:2 from amino acid 5 to amino acid 72.

18. The polynucleotide of claim 1, wherein the polynucleotide encodes a protein comprising a fragment of the amino acid sequence of SEQ ID NO:2, the fragment comprising the amino acid sequence of SEQ ID NO:2 from amino acid 28 to amino acid 115.

* * * * *

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 1790 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
CTGGTACCCA CCCCTGTCTC TGGACTTCTT TATGAACACT GAGTATTTGA CTCCCCACCC      60

TTCATGGTCA GCTCCTTTTA ACACCCTAGA TATCATTGCT GTCCTTTTCA TTGACATGCT     120

AGAGACATTT CCAATTTTCA TGGGAGTCAG TAAGATAGAG ATGATGAAAA TTCAGAGTGT     180

TCAAAGAAAG AGGAGGCCTC ATCAGTTGAT AGAATATACA ACAGATTGTC TAATCTCAGT     240
```

```
TTTCTTCACT TTTCTACCCA TTACAGTGGA AAAAAGAACC CTTAAGGAAG CCAGTGCTTC      300

TCAACATTGG TTACAAAACC ATCAGTGCCA GCACTTAATT TAAAATCTTC TGAAAATCCA      360

TCAGTTGGTT TTCATGTCTC ACTCTAAACT CAGCTCCAAC CAGGCTGCTT CCTAGATTCT      420

TGTCTGTGTG TGTTTCTGTT TTGGCTCTTT GTTACTTCCT TCTGTAAACT TAAGTAAACT      480

CAGTTTGTTG ACCTAGTGAA TTGATTCTTT CCATTTTCTA TACTATTCAC CAGCATATCA      540

AAGATGCTTC TTCCTAACTC TGATTTCCAG AGTAACTGTG CTATCAGCTT TCATACTAA       600

GAACTAGGTT TTTACCTTTT CACATTTCTT GCCTCCTACC CAGTTCGTAA GCCAAATTAG      660

ACTCGTACTC TTGTGAAGTG CCCTTTAGAT ACTAGTGTAA AATATACTGC GTAATTCTCC      720

ATTGCCCTAC ATATATTAAC CCTTTAAGAA AATATATCAC CAGTCTATTT TATCTTCGCA      780

GAACTTGCCC AGGTATGAGC CAGCATTTAT TACCACTCAT TCTAGAAGGT GCCAGTTAGG      840

TAGCTATCCA GGTTTACATT TTAAGGCAGT CGAGACCTTA TTCACGTGGT ATATAAACAA      900

CCACATTTCT CTTTTATATG GAACAAGACT TTTCATTTGC GGCTGGCCTT CTCACTAGCT      960

TATGCTTTTT TTTTTTAAGA CCTTTCTTAG CACTCGCTGA ACTCCTCCCC CTCACAATCA     1020

ATCTCAGCAA CTCAGCAGAG TCGCTTCAGT TCACAGCTCT TAATCCTTCA CTCCAGACTA     1080

AAGCTAATCT TATGTCCTCA AACAGCTACA ACTCACTGTT ATCACAGTTC CGACTGCAGA     1140

GACTCCATTT AAGAGGAAAT TTAAAAAATA AACAATGCTC TATTTCTGTC CACATCAAAG     1200

GTACCTCTAA CAGAAACTTG TCTTTGCTTC TGTCTCTCTG CTACTGGACT CTCAGCTCAA     1260

GGTAATGTAA GATGATCTCA TAGATGCACT TTAGCCTCTT GATGTTAGCA GTTGAGTCCT     1320

CCCTGCGCAC AAAATACATT TGTGGTAATG AATGCCCAGA ATCTCACTGG CACACCCAAG     1380

AGTAGTTAAA CTAAAATTGC TACTAACACA ACATTGTAGA ATTCGTTGCC TTAATGGATG     1440

TGATCTTCTA GGCTTACTGT GTCTTAACAA GCAGTCTTAT ATATATTTAT CTTGCCCAGA     1500

AAGTACACTT GTAGAATTTA ACATTTGCTC CTTTCTCCAA ACAGATTAAA GGTTATGCAG     1560

CTGAATGATT CTGTGTCCCA TTTTAAAGGT CCAGGCTATC CCCTAGATTT AGATTAGTTC     1620

CTAAAAAATC TTCCAGTCTG AATCCTGACA AATGGATAGC TAAATTAATT TCCACTCCTC     1680

TTCTCTCTTG CACTGTTTGG TACATTACAG CCACCATTAG CCTTAAAAGC TGCAGCAGCC     1740

AAATTCGGTG ACAGTAACAT AAAGCCTGAG CTTAAAAAAA AAAAAAAAA                 1790
```

(2) INFORMATION FOR SEQ ID NO:2:

(i) SEQUENCE CHARACTERISTICS:
        (A) LENGTH: 115 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

```
Met Glu Gln Asp Phe Ser Phe Ala Ala Gly Leu Leu Thr Ser Leu Cys
1               5                   10                  15

Phe Phe Phe Leu Arg Pro Phe Leu Ala Leu Ala Glu Leu Leu Pro Leu
                20                  25                  30

Thr Ile Asn Leu Ser Asn Ser Ala Glu Ser Leu Gln Phe Thr Ala Leu
            35                  40                  45

Asn Pro Ser Leu Gln Thr Lys Ala Asn Leu Met Ser Ser Asn Ser Tyr
        50                  55                  60

Asn Ser Leu Leu Ser Gln Phe Arg Leu Gln Arg Leu His Leu Arg Gly
65                  70                  75                  80
```

Asn Leu Lys Asn Lys Gln Cys Ser Ile Ser Val His Ile Lys Gly Thr
                85                  90                  95

Ser Asn Arg Asn Leu Ser Leu Leu Leu Ser Leu Cys Tyr Trp Thr Leu
            100                 105                 110

Ser Ser Arg
        115

(2) INFORMATION FOR SEQ ID NO:3:

(i) SEQUENCE CHARACTERISTICS:
        (A) LENGTH: 2026 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

| | | | | |
|---|---|---|---|---|
| CATTGAGTTG CCCTAACAAC ATTGTCTCCA GTGTCAGAAC CATATTAAGG TTCGTTTCTC | 60 |
| AGATTGGGAG CCTGCAACAC CATACAGCCA ACATTGCCTT TGCCACGCCA CTGCCACCAT | 120 |
| CCCCACCATT GCCCTATGGT GGGCAGATGA ATTCCAGAAA CCCTCAGGGA GCCAGGATAA | 180 |
| TTAGGCAACC CATCTGAATT GGCCACGTAA GTGACAGGCA CTTATCTCTC GGGTTCTTGC | 240 |
| TTTTGCAGAC TCCAGGGAAG TCCTGTCTAG AGGTCGATGG CAGAGACTCC TACTCTTTCC | 300 |
| CATGAGGGGT TGATAGGAAT CAAATTGGGA TTCCTTTGGC TTTGGGTTTT GTTTTTTTGT | 360 |
| TGTTGTTTTT GGTTTTCAGT TTGTTTTTTG GTGTATGGGG GGTGATTTTG TTTCTGAATA | 420 |
| AGAAAAAGAA GAGGCAACCA TGGCCCTTAT GTGGGTTTAT CCTTTTTGAG CAATGTTTTA | 480 |
| GCCACAAGTA AGGAATCTTG AAAGTCTTTT GTCCAGCAAG CAGTCTTAAA AATGTTTTTC | 540 |
| CTAACTCCTT TTGCAGGTGA CTAAGTACAA AAAAATAGTT TTCTCATTGT ATTCAAAATA | 600 |
| GTGAGTAGGT TCCCTGGATA ATACACAGTG GTAGTTGACA TATTTTCTCA AAACACAACC | 660 |
| AGAAAACCCA CTTCCGGTAT TTGTAAATCA CCTTTCAAGG GAAAAAGTGA ACACGTATTC | 720 |
| CTTGTATTTC TAGTTTGATT ACCAAACCTG ATGTTACAAA GAAACCTCCG TTCTGTAGAC | 780 |
| AGAATTTCTT TTATTTTTCT TCTTTTACTC CTCACAATCA CTTTCCCAGT GCCATCACCA | 840 |
| TCTATAAGGT CTCAGAGCAG AGGATTATTC ATGGTAATAA GTGGGGGTGT GGTGCAGCCA | 900 |
| TTCCAGTAAC ACCCACAAGA GGACAGCTGT TCTGAATGTC CCCACCCACC CCTCTTTCAG | 960 |
| TACAGGTGAG ACATTTTCAG TTCATGAGCT CCAGACCAAA TCCCAGGCCA GCCCTTGCAC | 1020 |
| CAAAAGCCTT TTTTAGAAGG CTTATCAGTC TATTAGGAAT GTCTCAGGAA AGATGAGCCA | 1080 |
| TTTCTTTGGG GAGAAATATA TTTACAGATG GAAGTGTGTG ACTGCGTGTC TGTGTGTGTG | 1140 |
| TGTGGTGTGT GTGCGCACGT GAGTGCGTGT GTTCATCTAT GTGCATTTCA CTTCCATAAA | 1200 |
| GACCCAGCCC AAGCTGCTGG GAACCATGTG TTCCTGAGTA TTCTCAGAGG TTAAACAAGT | 1260 |
| GACAAGTGAG CTTCTGAAAT TAGTGTCTCA GCAAGCTGGC TTTAGGAATG AGCCCCATTT | 1320 |
| TATCAAGCAG AGAAAAAAAA TAACAGCAGA AAAGATAAAG ATAAACCAAA AATATATACC | 1380 |
| CCCCAATGGA AAATAATGTT GATTCAGCAA TTCCCATAGG ATGTATTACA TGCTCTAATT | 1440 |
| TATTATATTA TTATTTATCT GTCTTTGATC TTTGCCCATT GTACTCTTAA AAAGATGTTG | 1500 |
| GGATGTTGAT TGCGATTTTT AAACAACTAG ATAATGTATA AATCAGCAGT GGAAATCAGT | 1560 |
| TTTAATGTGT GGATGTGTCT GATTATTGTT AAATGCCTCT TTTTTTACTT TTTTTTTTTT | 1620 |
| TAGATGTATA ATGTTTCATA AACCCTGGCA CTGGTCACAA AGCTCAGCTG TGAAAATGAA | 1680 |
| ATTTGTAGTA TTTTTAAACA TGAATGTCAA TTTCAAGTGT ATTTGAAATG GTTCCTCCAG | 1740 |

```
GAGAGATATT TGTGCACCAT TAGGAAAATC TTCTCTGCAG AGGAAGTAGC CTTCTTTGGA      1800

GAAAATGGAA AATGGGTTCT GATATGTGAT CTCAGAGTAG CCCATTTCCT AGGGCACCAT      1860

GGAAAACACA AATGTGATCT TTAAGTATAC CTCTTCCCCA GTTTGGGGAG GAAAGGACTC      1920

AGTTTGCACC CTTTTTGTAT GTAAAATAAA ATGTCTTACC TTTCTTGGCT AAAAAAAAAA      1980

AAAAAAAAAA AAAAAAAAAA AAAAAAAAAA AAAAAAAAAA AAAAA                     2026

(2) INFORMATION FOR SEQ ID NO:4:

(i) SEQUENCE CHARACTERISTICS:
         (A) LENGTH: 52 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO:4:

Met Leu Gln Arg Asn Leu Arg Ser Val Asp Arg Ile Ser Phe Ile Phe
1               5                   10                  15

Leu Leu Leu Leu Leu Thr Ile Thr Phe Pro Val Pro Ser Pro Ser Ile
            20                  25                  30

Arg Ser Gln Ser Arg Gly Leu Phe Met Val Ile Ser Gly Gly Val Val
        35                  40                  45

Gln Pro Phe Gln
    50

(2) INFORMATION FOR SEQ ID NO:5:

(i) SEQUENCE CHARACTERISTICS:
         (A) LENGTH: 1138 base pairs
         (B) TYPE: nucleic acid
         (C) STRANDEDNESS: double
         (D) TOPOLOGY: linear (ii) MOLECULE TYPE: cDNA (xi) SEQUENCE DESCRIPTION: SEQ ID NO:5:

GGGTCTGTGG AGAGCCGGGT GCGAGCGGCG GCAGCACGAG GGGAAAAGAG CTGAGCGGAG        60

ACCAAAGTCA GCCGGGAGAC AGTGGGTCTG TGAGAGACCG AATAGAGGGG CTGGGGCCAC       120

GAGCGCCATT GACAAGCAAT GGGGAAGAAA CAGAAAAACA AGAGCGAAGA CAGCACCAAG       180

GATGACATTG ATCTTGATGC CTTGGCTGCA GAAATAGAAG GAGCTGGTGC TGCCAAAGAA       240

CAGGAGCCTC AAAAGTCAAA AGGGAAAAAG AAAAAAGAGA AAAAAAAGCA GGACTTTGAT       300

GAAGATGATA TCCTGAAAGA ACTGGAAGAA TTGTCTTTGG AAGCTCAAGG CATCAAAGCT       360

GACAGAGAAA CTGTTGCAGT GAAGCCAACA GAAAACAATG AAGAGGAATT CACCTCAAAA       420

GATAAAAAAA AGAAAGGACA GAAGGGCAAA AAACAGAGTT TTGATGATAA TGATAGCGAA       480

GAATTGGAAG ATAAAGATTC AAAATCAAAA AAGACTGCAA AACCGAAAGT GGAAATGTAC       540

TCTGGGAGTG ATGATGATGA TGATTTTAAC AAACTTCCTA AAAAAGCTAA AGGGAAAGCT       600

CAAAAATCAA ATAAGAAGTG GGATGGGTCA GAGGAGGATG AGGATAACAG TAAAAAAATT       660

AAAGAGCGTT CAAGAATAAA TTCTTCTGGT GAAAGTGGTG ATGAATCAGA TGAATTTTTG       720

CAATCTAAAA GGACAGAAAA AAAATCAGAA AAACAAGCCA GGTCCTAACA TAGAAAGTGG       780

GAATGAAGAT GATGACGCCT CCTTCAAAAT TAAGACAGTG GCCCCAAAGA AGGCAGAAAA       840

GAAGGAGCGC GAGAGAAAAA AGCGAGATGA AGAAAAAGCG AAACTGCGGA AGCTGAAAGA       900

AAAAGAAGAG TTAGAAACAG GTAAAAAGGA TCAGAGTAAA CAAAAGGAAT CTCAAAGGAA       960
```

ATTTGAAGAA GAAACTGTAA AATCCAAAGT GACTGTTGAT ACTGGAGTAA TTCCTGCCTC    1020

TGAAGAGAAA GCAGAGACTC CCACAGCTGC AGAAGATGAC AATGAAGGAG ACAAAAAGAA    1080

GAAAGATAAG AAGAAAAAGA AAGGAGAAAA GGAAGAAAAA GAGAAAAAAA AAAAAAA       1138

(2) INFORMATION FOR SEQ ID NO:6:

(i) SEQUENCE CHARACTERISTICS:
        (A) LENGTH: 209 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Met Gly Lys Lys Gln Lys Asn Lys Ser Glu Asp Ser Thr Lys Asp Asp
1               5                   10                  15

Ile Asp Leu Asp Ala Leu Ala Ala Glu Ile Glu Gly Ala Gly Ala Ala
            20                  25                  30

Lys Glu Gln Glu Pro Gln Lys Ser Lys Gly Lys Lys Lys Glu Lys
        35                  40                  45

Lys Lys Gln Asp Phe Asp Glu Asp Ile Leu Lys Glu Leu Glu Glu
50                  55                  60

Leu Ser Leu Glu Ala Gln Gly Ile Lys Ala Asp Arg Glu Thr Val Ala
65                  70                  75                  80

Val Lys Pro Thr Glu Asn Asn Glu Glu Glu Phe Thr Ser Lys Asp Lys
                85                  90                  95

Lys Lys Lys Gly Gln Lys Gly Lys Lys Gln Ser Phe Asp Asp Asn Asp
            100                 105                 110

Ser Glu Glu Leu Glu Asp Lys Asp Ser Lys Ser Lys Lys Thr Ala Lys
        115                 120                 125

Pro Lys Val Glu Met Tyr Ser Gly Ser Asp Asp Asp Asp Phe Asn
130                 135                 140

Lys Leu Pro Lys Lys Ala Lys Gly Lys Ala Gln Lys Ser Asn Lys Lys
145                 150                 155                 160

Trp Asp Gly Ser Glu Glu Asp Glu Asp Asn Ser Lys Lys Ile Lys Glu
                165                 170                 175

Arg Ser Arg Ile Asn Ser Ser Gly Glu Ser Gly Asp Glu Ser Asp Glu
            180                 185                 190

Phe Leu Gln Ser Lys Arg Thr Glu Lys Lys Ser Glu Lys Gln Ala Arg
        195                 200                 205

Ser (2) INFORMATION FOR SEQ ID NO:7:

(i) SEQUENCE CHARACTERISTICS:
        (A) LENGTH: 912 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

ATCCAGCTCT TCAGAGAGA AGAGATGGGA ATAAGATAAG AACATCATTT CCTGAAGAGT    60

TTACTAAGTT GATGTTTTCT TTTGGTGAAG GGCAATGTGG AATTTAAATC ATATAGTTCA    120

TGTGTGCACC TGTCCTGCAG TTTGAGGCAG ATGATTTTAA ACCAGCATCT ATAGACACTT    180

```
CCTGTGAAGG AGAGCTTCAA GTTGGCAAAG GAGATGAAGT CACAATTACA CTGCCACATA      240

TCCCTAGCTG AGGGCAGCAG TAAAATCCAG GCCCGAATGG AACAGCAGCC CACTCGTCCT      300

CCACAGACGT CACAGCCACC ACCACCTCCA CCACCTATGC CATTCAGAGC TCCAACGAAG      360

CCTCCAGTTG GACCCAAAAC TTCTCCCTTG AAAGATAACC CGTCACCTGA ACCTCAGTTG      420

GATGACATCA AAAGAGAGCT GAGGGCTGAA GTTGACATTA TTGAACAAAT GAGCAGCAGC      480

AGTGGGAGCA GCTCTTCAGA CTCTGAGAGC TCTTCGGGAA GTGATGACGA TAGCTCCAGC      540

AGTGGAGGSG AGGAMAATGG CCCAGCYTCT CYTCCGCAGC YTTMACACCA GCAGCCYTAC      600

AACAGTAGGC CTGCCGTTGC CAATGGAACC AGCCGGCCAC AAGGAAGCAA CCAGYTYATG      660

AACACCCTCA GAAATGACTT GCAGTTGAGT GAGTYTGGCA GTGACAGTGA TGACTAGTGC      720

TGGATYTTTC GAAACCTACT TTTTGGTGCA CAAACATGCC GCAAGACTGA GCTACTTTGG      780

CCGTGGAGTC CATTGCAAGA GGAAAATGTT ATGGATCAGT GACTGTAGTA GGAGTTTGAG      840

GCTYTGGAAC TCTCACATAT TCAAGTCTTT AACTTAGTGG TGATGGGTGA AAAAAAAAA       900

AAAAAAAAAA AA                                                        912
```

(2) INFORMATION FOR SEQ ID NO:8:

(i) SEQUENCE CHARACTERISTICS:
        (A) LENGTH: 167 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

```
Met Lys Ser Gln Leu His Cys His Ile Ser Leu Ala Glu Gly Ser Ser
1               5                   10                  15

Lys Ile Gln Ala Arg Met Glu Gln Gln Pro Thr Arg Pro Pro Gln Thr
            20                  25                  30

Ser Gln Pro Pro Pro Pro Pro Pro Met Pro Phe Arg Ala Pro Thr
        35                  40                  45

Lys Pro Pro Val Gly Pro Lys Thr Ser Pro Leu Lys Asp Asn Pro Ser
    50                  55                  60

Pro Glu Pro Gln Leu Asp Asp Ile Lys Arg Glu Leu Arg Ala Glu Val
65                  70                  75                  80

Asp Ile Ile Glu Gln Met Ser Ser Ser Gly Ser Ser Ser Ser Asp
                85                  90                  95

Ser Glu Ser Ser Ser Gly Ser Asp Asp Ser Ser Ser Gly Gly
            100                 105                 110

Glu Xaa Asn Gly Pro Ala Ser Xaa Pro Gln Xaa Xaa His Gln Gln Pro
        115                 120                 125

Tyr Asn Ser Arg Pro Ala Val Ala Asn Gly Thr Ser Arg Pro Gln Gly
    130                 135                 140

Ser Asn Gln Xaa Met Asn Thr Leu Arg Asn Asp Leu Gln Leu Ser Glu
145                 150                 155                 160

Xaa Gly Ser Asp Ser Asp Asp
                165
```

(2) INFORMATION FOR SEQ ID NO:9:

(i) SEQUENCE CHARACTERISTICS:
        (A) LENGTH: 4582 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

```
GGTGAAGCTA ATCAAATCTG GTTCCTATGT AGCTCTCACT GTTCAGGGAC GCCCACCTGG      60
GTCGCCCCAG ATTCCACTTG CCGACTCTGA AGTAGAGCCG TCAGTCATTG GACATATGTC     120
TCCCATCATG ACATCTCCTC ATTCACCTGG AGCATCTGGG AATATGGAGA GAATCACTAG     180
TCCTGTGCTC ATGGGGAGG AAAACAATGT GGTTCATAAC CAGAAAGTAG AAATTCTGAG      240
AAAAATGTTA CAGAAAGAAC AGGAACGGCT ACAGTTATTG CAGGAAGATT ACAACCGAAC     300
ACCTGCCCAA AGATTGCTAA AAGAGATCCA AGAGGCCAAG AAACACATTC CTCAGCTGCA     360
AGAGCAGTTA TCCAAAGCCA CAGGCTCTGC TCAGGATGGA GCTGTAGTTA CACCCTCCAG     420
ACCTTTAGGG GACACCCTAA CAGTCAGTGA GGCAGAAACA GATCCTGGAG ATGTACTGGG     480
CAGGACTGAC TGTAGCAGTG GAGATGCTTC TCGGCCCAGT AGTGACAATG CAGATAGTCC     540
CAAGAGTGGC CCAAAAGAGA GAATTTATCT AGAGGAAAAC CCAGAGAAAA GTGAAACAAT     600
TCAGGACACT GACACTCAAT CACTTGTCGG AAGTCCCTCA ACCCGTATAG CACCTCATAT     660
TATTGGAGCA GAAGATGATG ATTTTGGTAC TGAACATGAA CAGATCAATG GACAGTGCAG     720
CTGTTTCCAG AGCATTGAAT TACTAAAATC TCGCCCGGCT CATTTGGCTG TTTTCTTACA     780
CCATGTAGTT TCACAATTTG ACCCTGCGAC TTTGCTCTGT TATCTCTATT CAGACCTGTA     840
TAAACATACC AATTCCAAAG AAACTCGTCG CATCTTCCTT GAGTTTCATC AGTTCTTTCT     900
AAATCGATCA GCACACCTGA AGTTTCTGT TCCTGATGAA ATGTCTGCAG ATCTAGAAAA      960
GAGAAGACCT GAGCTCATTC CTGAGGATCT GCATCGCCAC TATATCCAAA CTATGCAAGA    1020
AAGAGTCCAT CCAGAAGTTC AAAGGCACTT AAAAGATTTT CGGCAGAAAC GTAGTATGGG    1080
ACTGACCTTG GCTGAAAGCG AGCTGACTAA ACTTGATGCA GAGCGAGACA AGGACCGATT    1140
GACTTTGGAG AAGGAGCGGA CATGTGCAGA ACAGATTGTT GCCAAAATTG AAGAAGTATT    1200
GATGAYTGCT CAGGCTGTAR AGGAAGATAA GAGCTCCACC ATGCAGTATG TTATTCTCAT    1260
GTATATGAAG CATTTGGGAG TAAAAGTGAA AGAGCCTCGA AATTTGGAGC ACAAACGGGG    1320
TCGGATTGGA TTTCTTCCCA AAATCAAGCA AGTATGAAG AAAGATAAAG AAGGGGAAGA     1380
AAAAGGGAAG CGAAGAGGAT TCCCCAGCAT CCTGGGACCC CCACGGAGAC CAAGCCGTCA    1440
TGACAACAGT GCAATTGGCA GAGCCATGGA ACTACAGAAG GCGCGCCACC CTAAGCACTT    1500
ATCCACACCC TCATCTGTGA GTCCTGAACC TCAGGACTCT GCCAAGTTGC GCCAGAGTGG    1560
GTTAGCAAAT GAAGGAACAG ACGCTGGATA CCTGCCTGCC AATTCCATGT CTTCTGTAGC    1620
TTCAGGGGCC TCTTTTTCCC AGGAAGGAGG GAAAGAGAAT GATACAGGAT CAAAGCAAGT    1680
TGGAGAAACA TCAGCACCTG AGACACCTT AGATGGCACA CCTCGTACTC TCAATACTGT     1740
CTTTGATTTC CCACCACCTC CATTAGACCA AGTGCAGGAG GAGGAATGTG AAGTAGAAAG    1800
GGTGACTGAA CATGGGACAC CAAAGCCCTT TCGAAAGTTT GACAGTGTAG CTTTTGGAGA    1860
AAGTCAAAGT GAGGATGAAC AATTTGAAAA TGACTTAGAG ACAGATCCAC CCAACTGGCA    1920
GCAGCTTGTT AGTCGAGAAG TGTTACTGGG ACTAAAACCT TGTGAAATCA AAGACAGGA     1980
AGTGATTAAT GAATTGTTCT ACACTGAAAG AGCTCATGTT CGAACACTGA AGGTTCTTGA    2040
TCAAGTGTTC TATCAGCGAG TATCCAGAGA AGGAATTCTG TCACCCTCAG AGCTACGGAA    2100
AATTTTTTCA AACTTGGAAG ATATTCTTCA ACTTCATATT GGATTGAATG AACAAATGAA    2160
GGCTGTTCGA AAGAGAAATG AGACCTCTGT TATCGATCAG ATTGGGGAAG ATTTGCTGAC    2220
ATGGTTCAGC GGACCAGGAG AGGAGAAATT GAAACATGCT GCTGCTACCT TTTGCAGTAA    2280
```

```
CCAACCTTTC GCCCTGGAAA TGATCAAATC TCGTCAGAAA AAGGATTCTC GATTTCAGAC      2340

TTTTGTGCAA GATGCTGAAA GTAATCCACT GTGTCGTCGT CTTCAACTGA AGGATATTAT      2400

TCCCACTCAA ATGCAAAGGC TTACTAAGTA CCCACTTCTG TTGGATAATA TTGCCAAATA      2460

CACAGAATGG CCAACAGAAA GGGAGAAGGT GAAGAAAGCT GCAGATCACT GTCGTCAGAT      2520

CTTAAATTAT GTAAATCAGG CTGTCAAGGA GGCAGAAAAC AAGCAGCGCC TAGAAGATTA      2580

TCAGCGTCGC CTTGATACCT CCAGCCTGAA GTTGTCAGAG TACCCAAATG TTGAAGAGCT      2640

CAGGAATTTG GATTTAACAA AAAGGAAGAT GATTCATGAA GGGCCATTGG TTTGGAAGGT      2700

GAATAGAGAT AAAACTATTG ATTTATACAC GTTGCTGCTG GAAGACATTC TTGTATTGTT      2760

ACAAAAGCAG GATGATAGAC TGGTTTTAAG GTGTCATAGT AAGATTCTGG CATCTACAGC      2820

TGATAGCAAA CACACGTTTA GCCCTGTCAT TAAGTTGAGT ACAGTGTTGG TTCGACAAGT      2880

GGCAACAGAT AACAAAGCTT TATTCGTCAT TTCCATGTCA GACAATGGCG CTCAGATTTA      2940

TGAACTGGTG GCACAGACAG TTTCTGAAAA GACTGTCTGG CAGGACCTAA TCTGTCGGAT      3000

GGCTGCATCA GTGAAGGAGC AATCCACAAA GCCGATTCCA TTACCACAGT CAACACCTGG      3060

CGAAGGAGAT AATGATGAAG AAGATCCTTC AAAATTAAAA GAGGAGCAGC ATGGCATTTC      3120

AGTCACTGGT TTGCAGAGTC CAGACAGAGA TTTGGGATTA GAATCTACCT TAATATCGTC      3180

AAAACCTCAG TCTCATTCAC TGAGTACCTC TGGGAAATCA GAGGTACGTG ATCTGTTTGT      3240

GGCTGAGAGA CAGTTTGCAA GGAACAACA TACAGATGGG ACACTAAAGG AAGTTGGAGA      3300

AGATTATCAA ATCGCAATCC CAGATTCACA CCTGCCTGTC TCAGAAGAAC GGTGGGCATT      3360

GGATGCACTA AGAAATTTGG GTTTGTTGAA GCAGTTGCTG GTGCAACAGC TAGGTTTGAC      3420

TGAGAAGAGC GTTCAGGAAG ACTGGCAACA TTTCCCAAGA TACAGAACAG CCTCTCAGGG      3480

GCCGCAGACA GACAGTGTCA TCCAGAACTC TGAAAATATT AAGGCCTATC ATTCTGGTGA      3540

AGGACATATG CCCTTTAGAA CTGGAACTGG TGACATTGCA ACTTGTTACA GTCCACGGAC      3600

TTCAACTGAA TCTTTTGCTC CACGGGATTC AGTGGGACTG GCACCCCAGG ATAGCCAGGC      3660

AAGTAACATT TTAGTAATGG ACCACATGAT TATGACCCCA GAGATGCCTA CCATGGAGCC      3720

AGAAGGGGGT CTTGATGACA GTGGAGAGCA CTTTTTTGAT GCCCGTGAAG CACATAGTGA      3780

TGAGAATCCA TCAGAAGGTG ATGGAGCAGT TAACAAGGAA GAGAAGGATG TTAATTTACG      3840

CATCTCAGGA AACTATTTGA TCCTTGATGG CTATGACCCA GTGCAGGAGA GTTCCACAGA      3900

TGAGGAGGTT GCTTCCTCAC TTACCCTGCA GCCCATGACA GGCATCCCTG CTGTGGAATC      3960

CACCCACCAG CAGCAACATT CTCCTCAGAA TACTCACTCC GATGGGCAA TTTCACCATT      4020

CACCCCCGAA TTTCTGGTCC AGCAGCGCTG GGGAGCTATG GAGTATTCCT GTTTTGAGAT      4080

CCAGAGTCCC TCCTCTTGTG CAGATTCACA GAGCCAGATC ATGGAGTACA TTCATAAGAT      4140

AGAGGCTGAC CTTGAACACT TAAAGGAAGG TGGAGGAAAA TTAACACCAT TCTTTGCCAA      4200

AGGCTGGCTG GATCAGCCCT CACAGACAAG CACTCAGATA AAAGTTAGAG CCGCATGTCC      4260

TGGAGGTGAC TGCAGGTTGT TGGATTTGGA GTATCGGCCG TGTCTCACCA CATCCTGGCT      4320

CCAGTGTGGA TGCAGAGAGA GTGTGACAGA GGATCTGCCT GTGAACCACC TGGGATTAGT      4380

CAAGTCCCAA GGTGCCCAGA GTGGGACTAG TTYTTCACAG TGTGGCAGCT GCACTAATCT      4440

GTTTGTGAGG GAATATCCAT TCCCTCACTC TACTCTCCTC ACTATCGGAA ATTCATTTTG      4500

ATTCAGAATA AAACCAAAT GTATAGAGCT TTGGGTTGTA GGATATGAAA TTGTACTTAG      4560

ATTTAAGAAA AAAAAAAAAA AA                                               4582
```

(2) INFORMATION FOR SEQ ID NO:10:

(i) SEQUENCE CHARACTERISTICS:
        (A) LENGTH: 1461 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

```
Met Ser Pro Ile Met Thr Ser Pro His Ser Pro Gly Ala Ser Gly Asn
1               5                   10                  15

Met Glu Arg Ile Thr Ser Pro Val Leu Met Gly Glu Asn Asn Val
            20                  25                  30

Val His Asn Gln Lys Val Glu Ile Leu Arg Lys Met Leu Gln Lys Glu
        35                  40                  45

Gln Glu Arg Leu Gln Leu Leu Gln Glu Asp Tyr Asn Arg Thr Pro Ala
50                  55                  60

Gln Arg Leu Leu Lys Glu Ile Gln Glu Ala Lys Lys His Ile Pro Gln
65                  70                  75                  80

Leu Gln Glu Gln Leu Ser Lys Ala Thr Gly Ser Ala Gln Asp Gly Ala
                85                  90                  95

Val Val Thr Pro Ser Arg Pro Leu Gly Asp Thr Leu Thr Val Ser Glu
            100                 105                 110

Ala Glu Thr Asp Pro Gly Asp Val Leu Gly Arg Thr Asp Cys Ser Ser
        115                 120                 125

Gly Asp Ala Ser Arg Pro Ser Ser Asp Asn Ala Asp Ser Pro Lys Ser
130                 135                 140

Gly Pro Lys Glu Arg Ile Tyr Leu Glu Glu Asn Pro Glu Lys Ser Glu
145                 150                 155                 160

Thr Ile Gln Asp Thr Asp Thr Gln Ser Leu Val Gly Ser Pro Ser Thr
                165                 170                 175

Arg Ile Ala Pro His Ile Ile Gly Ala Glu Asp Asp Phe Gly Thr
            180                 185                 190

Glu His Glu Gln Ile Asn Gly Gln Cys Ser Cys Phe Gln Ser Ile Glu
        195                 200                 205

Leu Leu Lys Ser Arg Pro Ala His Leu Ala Val Phe Leu His His Val
210                 215                 220

Val Ser Gln Phe Asp Pro Ala Thr Leu Leu Cys Tyr Leu Tyr Ser Asp
225                 230                 235                 240

Leu Tyr Lys His Thr Asn Ser Lys Glu Thr Arg Arg Ile Phe Leu Glu
                245                 250                 255

Phe His Gln Phe Phe Leu Asn Arg Ser Ala His Leu Lys Val Ser Val
            260                 265                 270

Pro Asp Glu Met Ser Ala Asp Leu Glu Lys Arg Arg Pro Glu Leu Ile
        275                 280                 285

Pro Glu Asp Leu His Arg His Tyr Ile Gln Thr Met Gln Glu Arg Val
290                 295                 300

His Pro Glu Val Gln Arg His Leu Lys Asp Phe Arg Gln Lys Arg Ser
305                 310                 315                 320

Met Gly Leu Thr Leu Ala Glu Ser Glu Leu Thr Lys Leu Asp Ala Glu
                325                 330                 335

Arg Asp Lys Asp Arg Leu Thr Leu Glu Lys Glu Arg Thr Cys Ala Glu
            340                 345                 350

Gln Ile Val Ala Lys Ile Glu Glu Val Leu Met Xaa Ala Gln Ala Val
        355                 360                 365
```

-continued

```
Xaa Glu Asp Lys Ser Ser Thr Met Gln Tyr Val Ile Leu Met Tyr Met
    370                 375                 380

Lys His Leu Gly Val Lys Val Lys Glu Pro Arg Asn Leu Glu His Lys
385                 390                 395                 400

Arg Gly Arg Ile Gly Phe Leu Pro Lys Ile Lys Gln Ser Met Lys Lys
                405                 410                 415

Asp Lys Glu Gly Glu Lys Gly Lys Arg Arg Gly Phe Pro Ser Ile
                420                 425                 430

Leu Gly Pro Pro Arg Arg Pro Ser Arg His Asp Asn Ser Ala Ile Gly
            435                 440                 445

Arg Ala Met Glu Leu Gln Lys Ala Arg His Pro Lys His Leu Ser Thr
        450                 455                 460

Pro Ser Ser Val Ser Pro Glu Pro Gln Asp Ser Ala Lys Leu Arg Gln
465                 470                 475                 480

Ser Gly Leu Ala Asn Glu Gly Thr Asp Ala Gly Tyr Leu Pro Ala Asn
                485                 490                 495

Ser Met Ser Ser Val Ala Ser Gly Ala Ser Phe Ser Gln Glu Gly Gly
            500                 505                 510

Lys Glu Asn Asp Thr Gly Ser Lys Gln Val Gly Glu Thr Ser Ala Pro
        515                 520                 525

Gly Asp Thr Leu Asp Gly Thr Pro Arg Thr Leu Asn Thr Val Phe Asp
    530                 535                 540

Phe Pro Pro Pro Leu Asp Gln Val Gln Glu Glu Cys Glu Val
545                 550                 555                 560

Glu Arg Val Thr Glu His Gly Thr Pro Lys Pro Phe Arg Lys Phe Asp
                565                 570                 575

Ser Val Ala Phe Gly Glu Ser Gln Ser Glu Asp Glu Gln Phe Glu Asn
            580                 585                 590

Asp Leu Glu Thr Asp Pro Pro Asn Trp Gln Gln Leu Val Ser Arg Glu
        595                 600                 605

Val Leu Leu Gly Leu Lys Pro Cys Glu Ile Lys Arg Gln Glu Val Ile
610                 615                 620

Asn Glu Leu Phe Tyr Thr Glu Arg Ala His Val Arg Thr Leu Lys Val
625                 630                 635                 640

Leu Asp Gln Val Phe Tyr Gln Arg Val Ser Arg Glu Gly Ile Leu Ser
                645                 650                 655

Pro Ser Glu Leu Arg Lys Ile Phe Ser Asn Leu Glu Asp Ile Leu Gln
            660                 665                 670

Leu His Ile Gly Leu Asn Glu Gln Met Lys Ala Val Arg Lys Arg Asn
        675                 680                 685

Glu Thr Ser Val Ile Asp Gln Ile Gly Glu Asp Leu Leu Thr Trp Phe
690                 695                 700

Ser Gly Pro Gly Glu Glu Lys Leu Lys His Ala Ala Thr Phe Cys
705                 710                 715                 720

Ser Asn Gln Pro Phe Ala Leu Glu Met Ile Lys Ser Arg Gln Lys Lys
                725                 730                 735

Asp Ser Arg Phe Gln Thr Phe Val Gln Asp Ala Glu Ser Asn Pro Leu
            740                 745                 750

Cys Arg Arg Leu Gln Leu Lys Asp Ile Ile Pro Thr Gln Met Gln Arg
        755                 760                 765

Leu Thr Lys Tyr Pro Leu Leu Leu Asp Asn Ile Ala Lys Tyr Thr Glu
770                 775                 780

Trp Pro Thr Glu Arg Glu Lys Val Lys Lys Ala Ala Asp His Cys Arg
```

-continued

```
            785                 790                 795                 800
Gln Ile Leu Asn Tyr Val Asn Gln Ala Val Lys Glu Ala Glu Asn Lys
                    805                 810                 815
Gln Arg Leu Glu Asp Tyr Gln Arg Arg Leu Asp Thr Ser Ser Leu Lys
                    820                 825                 830
Leu Ser Glu Tyr Pro Asn Val Glu Leu Arg Asn Leu Asp Leu Thr
                    835                 840                 845
Lys Arg Lys Met Ile His Glu Gly Pro Leu Val Trp Lys Val Asn Arg
850                 855                 860
Asp Lys Thr Ile Asp Leu Tyr Thr Leu Leu Glu Asp Ile Leu Val
865                 870                 875                 880
Leu Leu Gln Lys Gln Asp Asp Arg Leu Val Leu Arg Cys His Ser Lys
                    885                 890                 895
Ile Leu Ala Ser Thr Ala Asp Ser Lys His Thr Phe Ser Pro Val Ile
                    900                 905                 910
Lys Leu Ser Thr Val Leu Val Arg Gln Val Ala Thr Asp Asn Lys Ala
                    915                 920                 925
Leu Phe Val Ile Ser Met Ser Asp Asn Gly Ala Gln Ile Tyr Glu Leu
                    930                 935                 940
Val Ala Gln Thr Val Ser Glu Lys Thr Val Trp Gln Asp Leu Ile Cys
945                 950                 955                 960
Arg Met Ala Ala Ser Val Lys Glu Gln Ser Thr Lys Pro Ile Pro Leu
                    965                 970                 975
Pro Gln Ser Thr Pro Gly Glu Gly Asp Asn Asp Glu Glu Asp Pro Ser
                    980                 985                 990
Lys Leu Lys Glu Glu Gln His Gly Ile Ser Val Thr Gly Leu Gln Ser
                    995                 1000                1005
Pro Asp Arg Asp Leu Gly Leu Glu Ser Thr Leu Ile Ser Ser Lys Pro
                    1010                1015                1020
Gln Ser His Ser Leu Ser Thr Ser Gly Lys Ser Glu Val Arg Asp Leu
1025                1030                1035                1040
Phe Val Ala Glu Arg Gln Phe Ala Lys Glu Gln His Thr Asp Gly Thr
                    1045                1050                1055
Leu Lys Glu Val Gly Glu Asp Tyr Gln Ile Ala Ile Pro Asp Ser His
                    1060                1065                1070
Leu Pro Val Ser Glu Glu Arg Trp Ala Leu Asp Ala Leu Arg Asn Leu
                    1075                1080                1085
Gly Leu Leu Lys Gln Leu Leu Val Gln Gln Leu Gly Leu Thr Glu Lys
                    1090                1095                1100
Ser Val Gln Glu Asp Trp Gln His Phe Pro Arg Tyr Arg Thr Ala Ser
1105                1110                1115                1120
Gln Gly Pro Gln Thr Asp Ser Val Ile Gln Asn Ser Glu Asn Ile Lys
                    1125                1130                1135
Ala Tyr His Ser Gly Glu Gly His Met Pro Phe Arg Thr Gly Thr Gly
                    1140                1145                1150
Asp Ile Ala Thr Cys Tyr Ser Pro Arg Thr Ser Thr Glu Ser Phe Ala
                    1155                1160                1165
Pro Arg Asp Ser Val Gly Leu Ala Pro Gln Asp Ser Gln Ala Ser Asn
                    1170                1175                1180
Ile Leu Val Met Asp His Met Ile Met Thr Pro Glu Met Pro Thr Met
1185                1190                1195                1200
Glu Pro Glu Gly Gly Leu Asp Asp Ser Gly Glu His Phe Phe Asp Ala
                    1205                1210                1215
```

```
Arg Glu Ala His Ser Asp Glu Asn Pro Ser Glu Gly Asp Gly Ala Val
            1220                1225                1230

Asn Lys Glu Glu Lys Asp Val Asn Leu Arg Ile Ser Gly Asn Tyr Leu
            1235                1240                1245

Ile Leu Asp Gly Tyr Asp Pro Val Gln Glu Ser Ser Thr Asp Glu Glu
            1250                1255                1260

Val Ala Ser Ser Leu Thr Leu Gln Pro Met Thr Gly Ile Pro Ala Val
1265                1270                1275                1280

Glu Ser Thr His Gln Gln Gln His Ser Pro Gln Asn Thr His Ser Asp
            1285                1290                1295

Gly Ala Ile Ser Pro Phe Thr Pro Glu Phe Leu Val Gln Gln Arg Trp
            1300                1305                1310

Gly Ala Met Glu Tyr Ser Cys Phe Glu Ile Gln Ser Pro Ser Ser Cys
            1315                1320                1325

Ala Asp Ser Gln Ser Gln Ile Met Glu Tyr Ile His Lys Ile Glu Ala
            1330                1335                1340

Asp Leu Glu His Leu Lys Glu Gly Gly Gly Lys Leu Thr Pro Phe Phe
1345                1350                1355                1360

Ala Lys Gly Trp Leu Asp Gln Pro Ser Gln Thr Ser Thr Gln Ile Lys
            1365                1370                1375

Val Arg Ala Ala Cys Pro Gly Gly Asp Cys Arg Leu Leu Asp Leu Glu
            1380                1385                1390

Tyr Arg Pro Cys Leu Thr Thr Ser Trp Leu Gln Cys Gly Cys Arg Glu
            1395                1400                1405

Ser Val Thr Glu Asp Leu Pro Val Asn His Leu Gly Leu Val Lys Ser
1410                1415                1420

Gln Gly Ala Gln Ser Gly Thr Ser Xaa Ser Gln Cys Gly Ser Cys Thr
1425                1430                1435                1440

Asn Leu Phe Val Arg Glu Tyr Pro Phe Pro His Ser Thr Leu Leu Thr
            1445                1450                1455

Ile Gly Asn Ser Phe
            1460

(2) INFORMATION FOR SEQ ID NO:11:

(i) SEQUENCE CHARACTERISTICS:
        (A) LENGTH: 2837 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

TCTTTTGACA GATATAATTG CTGCTTATCA AGATTCTGT TCTCGACCCC CAAAAGGATT      60

TGAAAAATAC TTTCCTAATG AAAAAATGG AAAAAAAGCT AGTGAACCTA AGAAGTTAT     120

GGGAGAGAAA AAAGAATCAA AGCCAGCTGC TACCACACGC TCTTCTGGAG GAGGAGGTGG   180

TGGCGGTGGA AAACGAGGTG GCAAGAAAGA TGATTCTCAC TGGTGGTCCA GGTTTCAGAA   240

GGGTGACATT CCATGGGACG ACAAGGATTT CAGGATGTTC TTCCTCTGGA CTGCTCTGTT   300

CTGGGGTGGA GTCATGTTTT ACTTGCTGCT CAAGAGATCC GGGAGAGAAA TCACTTGGAA   360

GGACTTTGTC AATAACTATC TTTCAAAAGG AGTAGTAGAC AGATTGGAAG TCGTCAACAA   420

GCGTTTTGTT CGAGTGACCT TTACACCAGG AAAAACTCCT GTTGATGGGC AATACGTTTG   480

GTTTAATATT GGCAGTGTGG ACACCTTTGA ACGGAATCTG GAAACTTTAC AGCAGGAATT   540

GGGCATAGAA GGAGAAAATC GGGTGCCTGT TGTCTACATT GCTGAAAGTG ATGGCTCTTT   600
```

```
TCTGCTGAGC ATGCTGCCTA CGGTGCTCAT CATCGCCTTC TTGCTCTACA CCATCAGAAG    660

AGGGCCTGCT GGCATTGGCC GGACAGGCCG AGGGATGGGC GGACTCTTCA GTGTCGGAGA    720

AACCACTGCC AAGGTCTTAA AGGATGAAAT TGATGTGAAG TTCAAAGATG TGGCTGGCTG    780

TGAGGAGGCC AAGCTAGAGA TCATGGAATT TGTGAATTTC TTGAAAAACC CAAAGCAGTA    840

TCAAGACCTA GGAGCAATAA TCCCAAAGGG TGCCATTCTC ACTGGTCCTC CAGGCACTGG    900

GAAGACGCTG CTAGCTAAGG CCACAGCCGG AGAAGCCAAT GTCCCCTTCA TCACCGTTAG    960

TGGATCTGAG TTTTTGGAGA TGTTCGTTGG TGTGGGCCCT GCTAGAGTCC GAGACTTATT   1020

TGCCCTTGCT CGGAAGAATG CCCCTTGCAT CCTCTTCATC GATGAAATCG ATGCGGTGGG   1080

AAGGAAGAGA GGAAGAGGCA ACTTTGGAGG GCAGAGTGAG CAGGAGAACA CACTCAACCA   1140

GCTGCTGGTG GAGATGGATG GTTTTAATAC AACAACAAAT GTCGTCATTT GGCCGGCAC    1200

CAATCGACCA GGACCACCAG ACATAAAAGG AAGAGCTTCT ATTTTCAAAG TTCATCTCCG   1260

ACCGCTAAAA CTGGACAGTA CCCTGGAGAA GGATAAATTG GCAAGAAAAC TGGCATCTTT   1320

AACTCCAGGG TTTTCAGGTG CTGATGTTGC TAATGTCTGT AATGAAGCTG CGTTGATTGC   1380

TGCAAGGCAT CTGTCAGATT CCATAAATCA GAAACACTTT GAACAGGCAA TTGAGCGAGT   1440

GATTGGTGGC TTAAAGAAAA AAACGCAGGT TCTGCAGCCT GAGGAGAAAA AGACTGTGGC   1500

ATACCACGAA GCAGGCCATG CGGTTGCCGG CTGGTATCTG GAGCACGCAG ACCCGCTTTT   1560

AAAGGTATCC ATCATCCCAC GTGGCAAAGG ACTAGGTTAT GCTCAGTATT TACCAAAAGA   1620

ACAATACCTC TATACCAAAG AGCAGCTCTT GGATAGGATG TGTATGACTT TAGGTGGTCG   1680

AGTCTCTGAA GAAATCTTCT TTGGAAGAAT TACAACTGGT GCTCAAGATG ACTTGAGAAA   1740

AGTAACTCAG AGTGCATATG CCCAAATTGT TCAGTTTGGC ATGAATGAAA AGGTTGGGCA   1800

AATCTCCTTT GACCTCCCAC GTCAGGGGGA CATGGTATTG GAGAAACCTT ACAGTGAAGC   1860

CACTGCAAGA TTGATAGATG ATGAAGTACG AATACTTATT AATGATGCTT ATAAAAGAAC   1920

AGTAGCTCTT CTCACAGAAA AGAAAGCTGA CGTGGAGAAG GTTGCTCTTC TGTTGTTAGA   1980

AAAAGAAGTA TTAGATAAGA ATGATATGGT TGAACTTTTG GGCCCCAGAC CATTTGCGGA   2040

AAAATCTACC TATGAAGAAT TTGTGGAAGG CACTGGCAGC TTGGATGAGG ACACCTCACT   2100

TCCAGAAGGC CTTAAGGACT GGAACAAGGA GCGGGAAAAG GAGAAAGAGG AGCCCCCGGG   2160

TGAGAAAGTT GCCAACTAGA GGCCCAGAGG GAGGCCATCT CAGTCTGTCC ACTGTGGTTT   2220

CAGCTGGTGC ATTATTTCAG CTGTGGCTTT CAGAAGAATG GGAATGCTGC GCTGATTTTA   2280

GCCAGCCACT GGCCCAGCTG AAATGATGGG GAAAGGAGTC CTTAGTCCTT TCAGCCTCAG   2340

AGGTCACAGT GGGTGGCAGG TGACTTTCCG GAGGCCTTGA GGGAAATGCA CACTGTCCCA   2400

TAGCCTCATT GGGTTCCCAG ACGTGCTGGA AAGGTTGAGC CCAGAGTGGC CGAGGCTGGA   2460

CCCTGTGGCA CCAAGTGGGG TCGGCTGACC GTGTGGCAGG GATTGTTGCA MTGGAWTTTT   2520

GGCGTGTGGG AAGGGATGCT TTTTTTTTGT CGCCCAYTTT TCATTCCTGT TTTTCCTCAG   2580

TTCCCCKGKG CAGATGGGCT GTGAAATTAA ATTGGAGTTT TGATAAGAAC ATTTTAATTT   2640

GACTTAATAT TTTAAAGATT GAATCCAGAT CACTTGTTGC TGTTTTAATG GAATGGTTTT   2700

TTACAGGAGC TGTAACATAM TTAAAAATAT GAATGTATTA TGTAAATATG GCTTCTTTAC   2760

ATAAAAAATA AAATGTCAAC ACTGTAAAAA AAAAAAAAAA AAAAAAAAAA AAAAAAAAAA   2820

AAAAAAAAAA AAAAAA                                                  2837
```

(2) INFORMATION FOR SEQ ID NO:12:

(i) SEQUENCE CHARACTERISTICS:
   (A) LENGTH: 686 amino acids
   (B) TYPE: amino acid
   (C) STRANDEDNESS:
   (D) TOPOLOGY: linear (ii) MOLECULE TYPE: protein (xi) SEQUENCE DESCRIPTION: SEQ ID NO:12:

```
Met Gly Glu Lys Lys Glu Ser Lys Pro Ala Ala Thr Thr Arg Ser Ser
 1               5                  10                  15

Gly Gly Gly Gly Gly Gly Gly Gly Lys Arg Gly Gly Lys Lys Asp Asp
            20                  25                  30

Ser His Trp Trp Ser Arg Phe Gln Lys Gly Asp Ile Pro Trp Asp Asp
            35                  40                  45

Lys Asp Phe Arg Met Phe Phe Leu Trp Thr Ala Leu Phe Trp Gly Gly
        50                  55                  60

Val Met Phe Tyr Leu Leu Leu Lys Arg Ser Gly Arg Glu Ile Thr Trp
 65                  70                  75                  80

Lys Asp Phe Val Asn Asn Tyr Leu Ser Lys Gly Val Val Asp Arg Leu
                85                  90                  95

Glu Val Val Asn Lys Arg Phe Val Arg Val Thr Phe Thr Pro Gly Lys
            100                 105                 110

Thr Pro Val Asp Gly Gln Tyr Val Trp Phe Asn Ile Gly Ser Val Asp
            115                 120                 125

Thr Phe Glu Arg Asn Leu Glu Thr Leu Gln Gln Glu Leu Gly Ile Glu
    130                 135                 140

Gly Glu Asn Arg Val Pro Val Val Tyr Ile Ala Glu Ser Asp Gly Ser
145                 150                 155                 160

Phe Leu Leu Ser Met Leu Pro Thr Val Leu Ile Ile Ala Phe Leu Leu
                165                 170                 175

Tyr Thr Ile Arg Arg Gly Pro Ala Gly Ile Gly Arg Thr Gly Arg Gly
            180                 185                 190

Met Gly Gly Leu Phe Ser Val Gly Glu Thr Thr Ala Lys Val Leu Lys
        195                 200                 205

Asp Glu Ile Asp Val Lys Phe Lys Asp Val Ala Gly Cys Glu Glu Ala
210                 215                 220

Lys Leu Glu Ile Met Glu Phe Val Asn Phe Leu Lys Asn Pro Lys Gln
225                 230                 235                 240

Tyr Gln Asp Leu Gly Ala Ile Ile Pro Lys Gly Ala Ile Leu Thr Gly
                245                 250                 255

Pro Pro Gly Thr Gly Lys Thr Leu Leu Ala Lys Ala Thr Ala Gly Glu
            260                 265                 270

Ala Asn Val Pro Phe Ile Thr Val Ser Gly Ser Glu Phe Leu Glu Met
        275                 280                 285

Phe Val Gly Val Gly Pro Ala Arg Val Arg Asp Leu Phe Ala Leu Ala
    290                 295                 300

Arg Lys Asn Ala Pro Cys Ile Leu Phe Ile Asp Glu Ile Asp Ala Val
305                 310                 315                 320

Gly Arg Lys Arg Gly Arg Gly Asn Phe Gly Gly Gln Ser Glu Gln Glu
                325                 330                 335

Asn Thr Leu Asn Gln Leu Leu Val Glu Met Asp Gly Phe Asn Thr Thr
            340                 345                 350

Thr Asn Val Val Ile Leu Ala Gly Thr Asn Arg Pro Gly Pro Pro Asp
        355                 360                 365

Ile Lys Gly Arg Ala Ser Ile Phe Lys Val His Leu Arg Pro Leu Lys
```

```
                   370              375              380
Leu Asp Ser Thr Leu Glu Lys Asp Lys Leu Ala Arg Lys Leu Ala Ser
385                  390              395              400

Leu Thr Pro Gly Phe Ser Gly Ala Asp Val Ala Asn Val Cys Asn Glu
                405              410              415

Ala Ala Leu Ile Ala Ala Arg His Leu Ser Asp Ser Ile Asn Gln Lys
                420              425              430

His Phe Glu Gln Ala Ile Glu Arg Val Ile Gly Gly Leu Lys Lys Lys
            435              440              445

Thr Gln Val Leu Gln Pro Glu Lys Lys Thr Val Ala Tyr His Glu
        450              455              460

Ala Gly His Ala Val Ala Gly Trp Tyr Leu Glu His Ala Asp Pro Leu
465              470              475              480

Leu Lys Val Ser Ile Ile Pro Arg Gly Lys Gly Leu Gly Tyr Ala Gln
                485              490              495

Tyr Leu Pro Lys Glu Gln Tyr Leu Tyr Thr Lys Glu Gln Leu Leu Asp
                500              505              510

Arg Met Cys Met Thr Leu Gly Gly Arg Val Ser Glu Glu Ile Phe Phe
            515              520              525

Gly Arg Ile Thr Thr Gly Ala Gln Asp Asp Leu Arg Lys Val Thr Gln
530              535              540

Ser Ala Tyr Ala Gln Ile Val Gln Phe Gly Met Asn Glu Lys Val Gly
545              550              555              560

Gln Ile Ser Phe Asp Leu Pro Arg Gln Gly Asp Met Val Leu Glu Lys
                565              570              575

Pro Tyr Ser Glu Ala Thr Ala Arg Leu Ile Asp Asp Glu Val Arg Ile
            580              585              590

Leu Ile Asn Asp Ala Tyr Lys Arg Thr Val Ala Leu Leu Thr Glu Lys
                595              600              605

Lys Ala Asp Val Glu Lys Val Ala Leu Leu Leu Glu Lys Glu Val
        610              615              620

Leu Asp Lys Asn Asp Met Val Glu Leu Leu Gly Pro Arg Pro Phe Ala
625              630              635              640

Glu Lys Ser Thr Tyr Glu Glu Phe Val Glu Gly Thr Gly Ser Leu Asp
                645              650              655

Glu Asp Thr Ser Leu Pro Glu Gly Leu Lys Asp Trp Asn Lys Glu Arg
            660              665              670

Glu Lys Glu Lys Glu Glu Pro Pro Gly Glu Lys Val Ala Asn
        675              680              685

(2) INFORMATION FOR SEQ ID NO:13:

(i) SEQUENCE CHARACTERISTICS:
        (A) LENGTH: 627 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:13:

GATTGGAGTT CTTTTCTTAA ATATCCAAAT AAGATTATAG CTATGTTTTT ACCAAATGTT       60

TGTGCGGTAA ATAGAGAGTG GATGGAAATT AACCCTAGAA AGGATAGTTG TAACTTTTAA      120

AAAGTTGATT AACTATTTCG TGTGCTAATT TGAGTTTTTC TGAATACTCC AATATGGTTT      180

CCTTTAACAC CTGCTCTCAG TTTACAATCA CCTAACTTCC CAGCGTTGGT GTCTTTTTCT      240
```

| | |
|---|---|
| CTGTCTGACC CTGTCTTATT TCTCCTACAA AGACATATCC TGCGCTGTAC TTCAGATACT | 300 |
| TTTTTCGAGG AACATTTGTG ATTTGTGGCA TAAAGTAACT GTCTAAAGGA AATCTTCTGA | 360 |
| GAGGATCTGG TCATTTTATG AAAGGGGCAA TTAAGGGGAA ATGGAAGCAG ATCTTTTAAA | 420 |
| GAAGGAGCAT TTGAAATTAG CCCAGGAATC ATGTCCGGCG AGTCCTGCTC TTTTGTACCT | 480 |
| GGGCATAATA GTCAGCCACA CAGAGCTAGA GTTAGTTCAA GAATTGTCTT TCCTGATCGT | 540 |
| GCTATATTTT TGGAAACACG TTAGATACAG AGGTAAGATG TCAAAATTCT GAAATACACA | 600 |
| CAATATAGGA TCAAAAAAAA AAAAAAA | 627 |

(2) INFORMATION FOR SEQ ID NO:14:

(i) SEQUENCE CHARACTERISTICS:
        (A) LENGTH: 63 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

```
Met Glu Ala Asp Leu Leu Lys Lys Glu His Leu Lys Leu Ala Gln Glu
  1               5                  10                  15

Ser Cys Pro Ala Ser Pro Ala Leu Leu Tyr Leu Gly Ile Ile Val Ser
             20                  25                  30

His Thr Glu Leu Glu Leu Val Gln Glu Leu Ser Phe Leu Ile Val Leu
         35                  40                  45

Tyr Phe Trp Lys His Val Arg Tyr Arg Gly Lys Met Ser Lys Phe
     50                  55                  60
```

(2) INFORMATION FOR SEQ ID NO:15:

(i) SEQUENCE CHARACTERISTICS:
        (A) LENGTH: 868 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:15:

| | |
|---|---|
| ATTCTGTCCC TGCCCTTAGA AAACCTAAAA TACCAAGGGT GTCATGCTGG CAACTCCCTG | 60 |
| CCCAGTCCTG CACAAAGCCT TGGCTGTGTG TGGCACCCCT TGCCTCCTAC CCAGAGCAG | 120 |
| CTGGCTCCAT TGGCTTCTCC CTGCACCAGC CCTGTCCTCA GGGGTCAGGA AAAAGCACAC | 180 |
| AGCTTTCTTT CCTCTCCTCC AGAGGCCTGG AAGGGAGGTG GAGGTCCAGT AAGGGCCTGG | 240 |
| CTGCCTTGGA TTTCTTGGTC CTGCCTTGCC AACTGCACCC TGTAGCTCCT GCTCCCTGTG | 300 |
| ACCCCAGAAC AGAGGTGCTG CCTTCCCTGT CTCCTAGACA AAGCACAAAG GGATGCCCTG | 360 |
| CTTGGCTTGA GCCTGCCCAA CTGAAGGATT TTCTCTGCCC CAGGGACCTT CCATCCCTGA | 420 |
| ATACAAGGCT CTAGGCAACT TCTCTCTGGG TGGTACACAC TAGAATGCCT GGCATTAGCC | 480 |
| CTAGAAAGGA GGTTGGGGTG TATGGGTAGT GAGCTAGGGT GGGAGAAAGG TGGTGCTGAA | 540 |
| AGGACAGATG CTAGTTGTAG TTTCACTCAC TCATTCATTC ATTAGTGCAA CAGTACTGAG | 600 |
| CACCACCTGC ACTAGAGGCA GAGGGGTGAA CAAGATACCC TTTTGCCTGG GGGACGTCC | 660 |
| ACTTCCCATG GGTTTGGCTA TTTCCAGGAA AGCCCCTCAG TCCTCCTCCC TGTTCTGGCT | 720 |
| GTGTGTGAAG GANGTGTGTG AGCAGGCCCA ATCCTTTGCA GCAAGAATGA GAGGTCAGAG | 780 |
| TATTCCATTG CACACGCACC CTGGGGCTGA CAGACTTGTG CCCCCTAGCC TTCATGCATG | 840 |

CCCAAGCACT GGCAGCTTTG CAGCCCCT                                               868

(2) INFORMATION FOR SEQ ID NO:16:

(i) SEQUENCE CHARACTERISTICS:
        (A) LENGTH: 107 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

```
Met Leu Val Val Val Ser Leu Thr His Ser Phe Ile Ser Ala Thr Val
 1               5                  10                  15

Leu Ser Thr Thr Cys Thr Arg Gly Arg Gly Val Asn Lys Ile Pro Phe
            20                  25                  30

Cys Leu Gly Gly Arg Pro Leu Pro Met Gly Leu Ala Ile Ser Arg Lys
        35                  40                  45

Ala Pro Gln Ser Ser Ser Leu Phe Trp Leu Cys Val Lys Xaa Val Cys
 50                  55                  60

Glu Gln Ala Gln Ser Phe Ala Ala Arg Met Arg Gly Gln Ser Ile Pro
 65                  70                  75                  80

Leu His Thr His Pro Gly Ala Asp Arg Leu Val Pro Pro Ser Leu His
                 85                  90                  95

Ala Cys Pro Ser Thr Gly Ser Phe Ala Ala Pro
                100                 105
```

(2) INFORMATION FOR SEQ ID NO:17:

(i) SEQUENCE CHARACTERISTICS:
        (A) LENGTH: 467 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:17:

TGGCTATCCC TAGAAGCACT TCATCCATCT TAACCCACCC AAACGGGATC CCTTCANATC    60

TCATACCCAG TAAGATGCAA GAAAGGAATA TTTGAGAGCA AGCAGCCCTG TTCCAGGGGC   120

CCCAGGTATG TGTAGAGGCC CAGTGGGGGT GGCCACTTGG TGTTTCTACC ACCCCCTGCC   180

ATCCAGTCTG GCCCAGTACC TACCTGGGAG GTTGGTGTAC TTGGCTTAAG TACTTCATGC   240

TTTATTCAGG CTGNTTCCCC ACAGCACCGG CAGGAAATGA AGGTGCACTT ATATGCATCC   300

CTGCAGGAAT AAAGAGTGGG TGGCCTGCCC AGCCCAGCAC CACAGCCTTT CCCCAGCCAG   360

GAGAGACCAC CTAAGGATCA AGGCAGCTCC TGTTTTCTTG GTTCTGTGAC ACTCGAGTCT   420

GAGCCAGCCC CTCAGGAATT GCCTCAAAAG AGAAAAAAAA AAAAAA                 467

(2) INFORMATION FOR SEQ ID NO:18:

(i) SEQUENCE CHARACTERISTICS:
        (A) LENGTH: 3831 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:18:

GCAGCAGGTC AAACAAGGCA TCTCCTAGTA TTGCATCCTA CAGATGTGCT GTAAACATCA    60

-continued

| | |
|---|---|
| AAAGAAGACG GTGGGATCAG GAGATGCTGT TTTGGAAAGA AGTGAGGTTT AGACTTCTCC | 120 |
| ATGTTAACCA TGAGCGTGAC ACTTTCCCCC CTGAGGTCAC AGGACCTGGA TCCCATGGCT | 180 |
| ACTGATGCTT CACCCATGGC CATCAACATG ACACCCACTG TGGAGCAGGG TGAGGGAGAA | 240 |
| GAGGCAATGA AGGACATGGA CTCTGACCAG CAGTATGAAA AGCCACCCCC ACTACACACA | 300 |
| GGGGCTGACT GGAAGATTGT CCTCCACTTA CCTGAAATTG AGACCTGGCT CCGGATGACC | 360 |
| TCAGAGAGGG TCCGAGACCT AACCTATTCA GTCCAGCAGG ATTCGGACAG CAAGCATGTG | 420 |
| GATGTACATC TAGTTCAACT AAAGGACATT TGTGAAGATA TTTCTGATCA TGTTGAGCAA | 480 |
| ATCCATGCCC TCCTTGAAAC AGAGTTCTCC CTAAAGCTGC TGTCTTACTC TGTCAACGTG | 540 |
| ATAGTGGACA TCCACGCAGT GCAGCTCCTC TGGCACCAGC TTCGAGTCTC AGTGCTGGTT | 600 |
| CTGCGGGAGC GCATTCTGCA AGGTCTGCAG GACGCCAATG GCAACTACAC TAGGCAGACG | 660 |
| GACATTCTGC AAGCTTTCTC TGAAGAGACA AAAGAGGGCC GGCTTGATTC TCTAACAGAA | 720 |
| GTGGATGACT CAGGACAATT AACCATCAAA TGTTCTCAAA ATTACTTGTC TCTGGATTGT | 780 |
| GGCATTACTG CATTCGAACT GTCTGACTAC AGTCCAAGTG AGGATTTGCT CAGTGGGCTA | 840 |
| GGTGACATGA CCTCTAGCCA AGTCAAAACC AAACCCTTTG ACTCTTGGAG CTACAGTGAG | 900 |
| ATGGAAAAGG AGTTTCCTGA GCTTATCCGA AGTGTTGGTT TACTTACGGT AGCTGCTGAC | 960 |
| TCTATCTCTA CCAATGGCAG TGAAGCAGTT ACTGAGGAGG TATCTCAAGT ATCTCTCTCA | 1020 |
| GTAGACGACA AAGGTGGATG TGAGGAAGAC AATGCTTCTG CAGTCGAAGA GCAACCAGGC | 1080 |
| TTAACACTGG GGGTGTCATC ATCTTCAGGA GAAGCTCTGA CAAATGCTGC TCAACCCTCC | 1140 |
| TCTGAGACTG TGCAGCAAGA ATCCAGTTCC TCCTCCCATC ATGATGCAAA GAATCAGCAG | 1200 |
| CCTGTTCCTT GTGAAAATGC AACCCCCAAA CGAACCATCA GAGATTGCTT TAATTATAAC | 1260 |
| GAGGACTCTC CCACACAGCC TACATTGCCA AAAAGAGGAC TTTTTCTTAA AGAGGAAACT | 1320 |
| TTTAAGAATG ATCTGAAAGG CAATGGTGGA AAGAGGCAAA TGGTTGATCT AAAGCCTGAG | 1380 |
| ATGAGCAGAA GCACCCCTTC GCTAGTAGAT CCTCCTGACA GATCCAAACT TTGCCTGGTA | 1440 |
| TTGCAGTCTT CTTACCCCAA CAGCCCTTCT GCTGCCAGCC AGTCTTATGA GTGTTTACAC | 1500 |
| AAGGTGGGGA ATGGGAACCT TGAAAACACA GTCAAATTTC ACATTAAAGA AATTTCTTCC | 1560 |
| AGCCTGGGAA GGCTTAACGA CTGCTATAAA GAGAAATCTC GACTTAAAAA GCCACACAAG | 1620 |
| ACCTCAGAAG AGGTGCCTCC ATGCCGAACA CCTAAACGGG GGACTGGTTC AGGCAAACAA | 1680 |
| GCTAAAAATA CAAAGAGCTC AGCAGTGCCA AATGGAGAGC TTTCTTATAC TTCCAAGGCC | 1740 |
| ATAGAGGGGC CACAAACAAA TTCTGCTTCC ACATCCTCAC TTGAGCCTTG TAATCAGAGA | 1800 |
| AGTTGGAATG CCAAATTGCA ATTGCAGTCA GAAACATCCA GTTCACCAGC TTTTACTCAG | 1860 |
| AGCAGTGAAT CCTCTGTTGG CTCAGACAAC ATCATGTCTC CGGTGCCACT TCTTTCAAAA | 1920 |
| CACAAAAGCA AAAAGGTCA AGCCTCCTCT CCAAGTCACG TCACTAGGAA TGGTGAGGTT | 1980 |
| GTGGAGGCCT GGTATGGCTC TGATGAATAC CTAGCACTGC CCTCTCACCT TAAGCAGACA | 2040 |
| GAAGTATTGG CTTTGAAGTT GGAAAACCTA ACAAAGCTTC TGCCTCAGAA ACCCAGAGGA | 2100 |
| GAAACCATCC AGAATATTGA TGACTGGGAA CTGTCTGAAA TGAATTCAGA TTCTGAAATC | 2160 |
| TATCCAACCT ATCATGTCAA AAAGAAGCAT ACAAGGCTAG GCAGGGTGTC TCCAAGCTCA | 2220 |
| TCTAGTGACA TAGCCTCTTC ACTAGGGGAG AGCATTGAAT CTGGGCCCCT GAGTGACATT | 2280 |
| CTTTCTGATG AGGAGTCCAG TATGCCTCTC GCTGGCATGA AAAGTATGC TGATGAGAAG | 2340 |
| TCAGAAAGAG CTTCATCCTC TGAGAAAAAT GAGAGCCATT CTGCCACTAA ATCAGCTTTA | 2400 |
| ATTCAGAAAC TGATGCAAGA TATTCAGCAC CAAGACAACT ATGAAGCCAT ATGGGAAAAA | 2460 |

```
ATAGAGGGGT TGTAAACAA ACTGGATGAA TTCATTCAAT GGTTAAATGA AGCCATGGAA    2520

ACTACAGAGA ATTGGACTCC CCCTAAAGCA GAGATGGATG ACCTTAAACT GTATCTGGAG    2580

ACACACTTGA GTTTTAAGTT GAATGTAGAC AGTCATTGTG CTCTCAAGGA AGCTGTGGAG    2640

GAGGAAGGAC ACCAACTTCT TGAGCTTATT GCATCTCACA AAGCAGGACT GAAGGACATG    2700

CTGCGGATGA TTGCAAGTCA ATGGAAGGAG CTGCAGAGGC AAATCAAACG GCAGCACAGC    2760

TGGATTCTCA GGGCTCTGGA TACCATCAAA GCCGAGATAC TGGCTACTGA TGTGTCTGTG    2820

GAGGATGAGG AAGGGACTGG AAGCCCCAAG GCTGAGGTTC AACTATGCTA CCTGGAAGCA    2880

CAAAGAGATG CTGTTGAGCA GATGTCCCTC AAGCTGTACA GCGAGCAGTA TACCAGCAGC    2940

AGCAAGCGAA AGGAAGAGTT TGCTGATATG TCAAAAGTTC ATTCAGTGGG AAGCAATGGG    3000

CTTCTGGACT TTGATTCAGA ATATCAGGAG CTCTGGGATT GGCTGATTGA CATGGAGTCC    3060

CTTGTGATGG ACAGCCACGA CCTGATGATG TCAGAGGAGC AGCAGCAGCA TCTTTACAAG    3120

CGATACAGTG TGGAAATGTC CATCAGACAC CTGAAAAAGA CGGAGCTGCT TAGTAAGGTT    3180

GAAGCTTTGA AGAAAGGTGG CGTTTTACTA CCAAATGATC TCCTTGAAAA AGTGGATTCA    3240

ATTAATGAAA AATGGGAACT GCTTGGGGTA TTTGCATTTT TATTACTGTT TGTAGGTTAT    3300

GTGTACATTT TTTGCGTAGT GAAGTACTCT GTCCGATTTC TAATTTGAGG CACAAATATC    3360

TCTCTCTTTC AATTCACTAC CTACGTTTCA AACAAGCTAT TCATGCTATT ATGGGAAAGA    3420

CACTGCTTTT CCTCTTCTGT TGATTTTTTT TTTTTCTGAG CTTGTCCCCT CTCAGATTTT    3480

AATAATTTTG GTTCTTTAAT ACATGAAAAA GTAAGTAAAA TATGCCATGT ATTATGGGTA    3540

TGCACCAAGT CAACTATAAT ACAGTATATC TGATATATAC TGACTGTCAT GCTTGAATGA    3600

ATGTTAATAG AATTTATTCT GAAGGTACAT GTGAGAGACA TCTACTGTTT AACTATTTAC    3660

TGTACCCTTA AGATGAAAAG TGGAGTTGTC ACTACAGCTT TCAAGTCACA CTAAAGCCAC    3720

CAAAACAAAG ATGCAAATTT GACCCAAATC TGAATTGCAG AATTGAATCA GCCTGTGTTT    3780

TGTGCCTCAA TTTCCAGCTC ACTTTTAACA AAAGCCAAAA AAAAAAAAA A              3831
```

(2) INFORMATION FOR SEQ ID NO:19:

(i) SEQUENCE CHARACTERISTICS:
        (A) LENGTH: 1075 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:19:

```
Met Leu Thr Met Ser Val Thr Leu Ser Pro Leu Arg Ser Gln Asp Leu
1               5                  10                  15

Asp Pro Met Ala Thr Asp Ala Ser Pro Met Ala Ile Asn Met Thr Pro
            20                  25                  30

Thr Val Glu Gln Gly Glu Gly Glu Ala Met Lys Asp Met Asp Ser
        35                  40                  45

Asp Gln Gln Tyr Glu Lys Pro Pro Leu His Thr Gly Ala Asp Trp
    50                  55                  60

Lys Ile Val Leu His Leu Pro Glu Ile Glu Thr Trp Leu Arg Met Thr
65                  70                  75                  80

Ser Glu Arg Val Arg Asp Leu Thr Tyr Ser Val Gln Gln Asp Ser Asp
                85                  90                  95

Ser Lys His Val Asp Val His Leu Val Gln Leu Lys Asp Ile Cys Glu
            100                 105                 110
```

```
Asp Ile Ser Asp His Val Glu Gln Ile His Ala Leu Leu Glu Thr Glu
        115                 120                 125

Phe Ser Leu Lys Leu Leu Ser Tyr Ser Val Asn Val Ile Val Asp Ile
    130                 135                 140

His Ala Val Gln Leu Leu Trp His Gln Leu Arg Val Ser Val Leu Val
145                 150                 155                 160

Leu Arg Glu Arg Ile Leu Gln Gly Leu Gln Asp Ala Asn Gly Asn Tyr
                165                 170                 175

Thr Arg Gln Thr Asp Ile Leu Gln Ala Phe Ser Glu Thr Lys Glu
                180                 185                 190

Gly Arg Leu Asp Ser Leu Thr Glu Val Asp Asp Ser Gly Gln Leu Thr
        195                 200                 205

Ile Lys Cys Ser Gln Asn Tyr Leu Ser Leu Asp Cys Gly Ile Thr Ala
    210                 215                 220

Phe Glu Leu Ser Asp Tyr Ser Pro Ser Glu Asp Leu Leu Ser Gly Leu
225                 230                 235                 240

Gly Asp Met Thr Ser Ser Gln Val Lys Thr Lys Pro Phe Asp Ser Trp
                245                 250                 255

Ser Tyr Ser Glu Met Glu Lys Glu Phe Pro Glu Leu Ile Arg Ser Val
                260                 265                 270

Gly Leu Leu Thr Val Ala Ala Asp Ser Ile Ser Thr Asn Gly Ser Glu
        275                 280                 285

Ala Val Thr Glu Glu Val Ser Gln Val Ser Leu Ser Val Asp Asp Lys
    290                 295                 300

Gly Gly Cys Glu Glu Asp Asn Ala Ser Ala Val Glu Glu Gln Pro Gly
305                 310                 315                 320

Leu Thr Leu Gly Val Ser Ser Ser Gly Glu Ala Leu Thr Asn Ala
                325                 330                 335

Ala Gln Pro Ser Ser Glu Thr Val Gln Gln Glu Ser Ser Ser Ser Ser
        340                 345                 350

His His Asp Ala Lys Asn Gln Gln Pro Val Pro Cys Glu Asn Ala Thr
    355                 360                 365

Pro Lys Arg Thr Ile Arg Asp Cys Phe Asn Tyr Asn Glu Asp Ser Pro
    370                 375                 380

Thr Gln Pro Thr Leu Pro Lys Arg Gly Leu Phe Leu Lys Glu Glu Thr
385                 390                 395                 400

Phe Lys Asn Asp Leu Lys Gly Asn Gly Gly Lys Arg Gln Met Val Asp
                405                 410                 415

Leu Lys Pro Glu Met Ser Arg Ser Thr Pro Ser Leu Val Asp Pro Pro
                420                 425                 430

Asp Arg Ser Lys Leu Cys Leu Val Leu Gln Ser Ser Tyr Pro Asn Ser
        435                 440                 445

Pro Ser Ala Ala Ser Gln Ser Tyr Glu Cys Leu His Lys Val Gly Asn
    450                 455                 460

Gly Asn Leu Glu Asn Thr Val Lys Phe His Ile Lys Glu Ile Ser Ser
465                 470                 475                 480

Ser Leu Gly Arg Leu Asn Asp Cys Tyr Lys Glu Lys Ser Arg Leu Lys
                485                 490                 495

Lys Pro His Lys Thr Ser Glu Glu Val Pro Pro Cys Arg Thr Pro Lys
                500                 505                 510

Arg Gly Thr Gly Ser Gly Lys Gln Ala Lys Asn Thr Lys Ser Ser Ala
        515                 520                 525

Val Pro Asn Gly Glu Leu Ser Tyr Thr Ser Lys Ala Ile Glu Gly Pro
    530                 535                 540
```

-continued

```
Gln Thr Asn Ser Ala Ser Thr Ser Ser Leu Glu Pro Cys Asn Gln Arg
545                 550                 555                 560

Ser Trp Asn Ala Lys Leu Gln Leu Gln Ser Glu Thr Ser Ser Ser Pro
                565                 570                 575

Ala Phe Thr Gln Ser Ser Glu Ser Ser Val Gly Ser Asp Asn Ile Met
            580                 585                 590

Ser Pro Val Pro Leu Leu Ser Lys His Lys Ser Lys Lys Gly Gln Ala
        595                 600                 605

Ser Ser Pro Ser His Val Thr Arg Asn Gly Glu Val Val Glu Ala Trp
    610                 615                 620

Tyr Gly Ser Asp Glu Tyr Leu Ala Leu Pro Ser His Leu Lys Gln Thr
625                 630                 635                 640

Glu Val Leu Ala Leu Lys Leu Glu Asn Leu Thr Lys Leu Leu Pro Gln
                645                 650                 655

Lys Pro Arg Gly Glu Thr Ile Gln Asn Ile Asp Asp Trp Glu Leu Ser
            660                 665                 670

Glu Met Asn Ser Asp Ser Glu Ile Tyr Pro Thr Tyr His Val Lys Lys
        675                 680                 685

Lys His Thr Arg Leu Gly Arg Val Ser Pro Ser Ser Ser Asp Ile
    690                 695                 700

Ala Ser Ser Leu Gly Glu Ser Ile Glu Ser Gly Pro Leu Ser Asp Ile
705                 710                 715                 720

Leu Ser Asp Glu Glu Ser Ser Met Pro Leu Ala Gly Met Lys Lys Tyr
                725                 730                 735

Ala Asp Glu Lys Ser Glu Arg Ala Ser Ser Glu Lys Asn Glu Ser
            740                 745                 750

His Ser Ala Thr Lys Ser Ala Leu Ile Gln Lys Leu Met Gln Asp Ile
        755                 760                 765

Gln His Gln Asp Asn Tyr Glu Ala Ile Trp Glu Lys Ile Glu Gly Phe
    770                 775                 780

Val Asn Lys Leu Asp Glu Phe Ile Gln Trp Leu Asn Glu Ala Met Glu
785                 790                 795                 800

Thr Thr Glu Asn Trp Thr Pro Pro Lys Ala Glu Met Asp Asp Leu Lys
                805                 810                 815

Leu Tyr Leu Glu Thr His Leu Ser Phe Lys Leu Asn Val Asp Ser His
            820                 825                 830

Cys Ala Leu Lys Glu Ala Val Glu Glu Gly His Gln Leu Leu Glu
        835                 840                 845

Leu Ile Ala Ser His Lys Ala Gly Leu Lys Asp Met Leu Arg Met Ile
    850                 855                 860

Ala Ser Gln Trp Lys Glu Leu Gln Arg Gln Ile Lys Arg Gln His Ser
865                 870                 875                 880

Trp Ile Leu Arg Ala Leu Asp Thr Ile Lys Ala Glu Ile Leu Ala Thr
                885                 890                 895

Asp Val Ser Val Glu Asp Glu Gly Thr Gly Ser Pro Lys Ala Glu
            900                 905                 910

Val Gln Leu Cys Tyr Leu Glu Ala Gln Arg Asp Ala Val Glu Gln Met
        915                 920                 925

Ser Leu Lys Leu Tyr Ser Glu Gln Tyr Thr Ser Ser Ser Lys Arg Lys
    930                 935                 940

Glu Glu Phe Ala Asp Met Ser Lys Val His Ser Val Gly Ser Asn Gly
945                 950                 955                 960

Leu Leu Asp Phe Asp Ser Glu Tyr Gln Glu Leu Trp Asp Trp Leu Ile
```

```
                    965              970              975
Asp Met Glu Ser Leu Val Met Asp Ser His Asp Leu Met Met Ser Glu
                980              985              990

Glu Gln Gln Gln His Leu Tyr Lys Arg Tyr Ser Val Glu Met Ser Ile
        995              1000             1005

Arg His Leu Lys Lys Thr Glu Leu Leu Ser Lys Val Glu Ala Leu Lys
    1010             1015             1020

Lys Gly Gly Val Leu Leu Pro Asn Asp Leu Leu Glu Lys Val Asp Ser
1025             1030             1035             1040

Ile Asn Glu Lys Trp Glu Leu Leu Gly Val Phe Ala Phe Leu Leu Leu
                1045             1050             1055

Phe Val Gly Tyr Val Tyr Ile Phe Cys Val Val Lys Tyr Ser Val Arg
                1060             1065             1070

Phe Leu Ile
        1075

(2) INFORMATION FOR SEQ ID NO:20:

(i) SEQUENCE CHARACTERISTICS:
        (A) LENGTH: 3113 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:20:

GCAAACACAT TGAAGTACAG GTAGCCCAGG AAACTAGAAA TGTATCTACT GGCTCTGCTG      60

AAAATGAAGA AAAGTCAGAA GTTCAAGCAA TCATCGAATC TACTCCTGAG CTGGATATGG    120

ACAAAGATCT CAGTGGATAT AAAGGTTCAA GCACTCCCAC CAAAGGCATA GAGAACAAAG    180

CTTTTGATCG CAATACAGAA TCTCTCTTTG AAGAACTGTC TTCAGCTGGC TCAGGCCTAA    240

TAGGAGATGT GGATGAAGGA GCAGATTTAC TAGGAATGGG TCGGGAAGTT GAGAATCTTA    300

TATTAGAAAA TACACAACTG TTGGAAACCA AAAATGCTTT GAACATAGTG AAGAATGATT    360

TGATAGCAAA AGTGGATGAA CTGACCTGTG AGAAAGATGT GCTGCAAGGG GAATTGGAGG    420

CTGTGAAGCA AGCCAAACTG AAACTAGAGG AAAAGAACAG AGAATTGGAG GAAGAGCTTA    480

GGAAAGCTCG GGCAGAAGCT GAAGATGCAG GGCAAAAAGC AAAAGATGAC GATGATAGTG    540

ATATTCCCAC AGCCCAGAGG AAACGGTTTA CTAGAGTAGA AATGGCCCGT GTTCTCATGG    600

AGCGAAACCA GTATAAAGAG AGATTGATGG AGCTTCAGGA AGCTGTTCGA TGGACAGAGA    660

TGATTCGGGC ATCACGAGAA AATCCAGCCA TGCAGGAAAA AAAAAGGTCA AGCATTTGGC    720

AGTTTTTCAG CCGACTTTTC AGCTCCTCAA GTAACACGAC TAAGAAGCCT GAACCACCTG    780

TTAATCTGAA GTACAATGCA CCCACGTCTC ATGTTACTCC GTCCGTCAAG AAAAGAAGCA    840

GCACCTTATC TCAGCTCCCT GGGGATAAGT CCAAAGCCTT TGATTTCCTT AGTGAAGAAA    900

CTGAAGCTAG TTTAGCCTCA CGCAGAGAAC AAAAGAGAGA GCAGTATCGT CAGGTAAAAG    960

CACATGTTCA GAAGGAAGAC GGTAGAGTGC AGGCTTTTGG CTGGAGTCTG CCTCAGAAGT   1020

ACAAACAGGT AACCAATGGT CAAGGTGAAA ATAAGATGAA AAATTTACCT GTGCCTGTCT   1080

ATCTCAGACC TCTGGATGAA AAAGATACAT CAATGAAGCT GTGGTGTGCT GTTGGAGTCA   1140

ATTTATCTGG TGGGAAGACC AGAGATGGTG GTTCTGTTGT TGGAGCAAGT GTATTTTACA   1200

AGGATGTTGC TGGTTTGGAT ACAGAAGGCA GTAAACAGCG AAGTGCCTCT CAGAGTAGTT   1260

TAGATAAGTT AGATCAGGAA CTTAAGGAAC AGCAGAAGGA GTTAAAAAAT CAAGAAGAAT   1320
```

```
TATCCAGTCT AGTTTGGATC TGTACCAGCA CTCATTCGGC TACAAAAGTT CTTATTATTG    1380

ATGCTGTTCA ACCTGGCAAC ATCCTAGACA GTTTCACTGT TTGCAACTCT CATGTTCTGT    1440

GCATTGCAAG TGTGCCAGGT GCACGAGAAA CAGACTACCC TGCAGGAGAA GATCTTTCAG    1500

AATCTGGTCA GGTAGACAAA GCATCTTTAT GTGGAAGTAT GACAAGCAAC AGCTCAGCAG    1560

AGACAGACAC CCTGTTAGGA GGCATCACAG TGGTTGGTTG TTCTGCAGAA GGTGTGACGG    1620

GAGCTGCCAC TTCCCCTAGT ACAAATGGTG CTTCTCCAGT GATGGATAAA CCACCAGAAA    1680

TGGAAGCAGA AAATAGTGAG GTTGATGAAA ATGTTCCAAC AGCAGAAGAA GCAACTGAAG    1740

CTACAGAAGG GAATGCGGGG TCAGCTGAAG ACACAGTGGA CATCTCCCAA ACTGGCGTCT    1800

ACACAGAGCA TGTCTTTACA GATCCTTTGG GAGTTCAGAT CCCAGAAGAC CTCTCCCCAG    1860

TGTATCAGTC GAGCAATGAC TCAGATGCAT ATAAAGATCA AATATCAGTA CTGCCAAATG    1920

AACAAGACTT GGTGAGAGAA GAAGCCCAGA AAATGAGTAG TCTTTTACCA ACTATGTGGC    1980

TTGGAGCTCA AAATGGCTGT TTGTATGTCC ATTCATCTGT AGCCCAGTGG AGGAAATGTC    2040

TCCATTCCAT TAAACTTAAA GATTCGATTC TCAGTATTGT ACACGTGAAG GGAATCGTGT    2100

TAGTAGCCCT GGCTGACGGC ACCCTTGCAA TCTTTCACAG AGGAGTGGAT GGGCAGTGGG    2160

ATTTGTCAAA CTATCACCTC TTAGACCTTG GACGGCCTCA TCATTCCATC CGTTGCATGA    2220

CTGTGGTACA TGACAAAGTC TGGTGTGGCT ATAGGAACAA AATCTATGTG GTGCAGCCAA    2280

AGGCCATGAA AATAGAGAAA TCTTTTGATG CACATCCCAG GAAGGAGAGC CAAGTGCGAC    2340

AGCTTGCGTG GGTGGGGGAT GGCGTGTGGG TCTCCATTCG CTTGGATTCT ACGCTCCGTC    2400

TCTATCATGC ACACACTTAT CAACATCTAC AGGATGTGGA CATTGAGCCT TATGTAAGCA    2460

AAATGTTAGG TACTGGAAAA CTGGGCTTCT CTTTTGTGAG AATTACAGCT CTTATGGTGT    2520

CTTGTAATCG TTTGTGGGTG GGGACAGGAA ATGGTGTCAT TATCTCCATC CCATTGACAG    2580

AAAGTAAGTA TATTTTTAGA TAACTGCCAT GGAACAAATA GGAGAATTAT AGGAAATAGT    2640

TATGTCTGAA ATTCAAATCT GTGTTAGCTC AAGAAAATCA GTGATGGCAA AGATCTAGCT    2700

ATAGTTAACT TCAACTCAAT GAAACTTATA AATTCTAGGA AAATAAGTTT TCATGTATCA    2760

AGACCAATAC TCATAATTAA AAGTTTTTCG TTGTCAAAAC ATTTTCACAG TTCAGGAATC    2820

ACAGTCCTAT TTCATCTTTT GAAATAAAAG TTAAAGTCCA TTTTTCTTAA GCCTTATTAT    2880

ACCATTATCC AAAAACACTA CCTAGCATTC ATCTTAGTTT TTCATATCTC CTTAGCAGAT    2940

AGTTTAGTAT ATTCCATTTG TCTTATTTGA GGTTTAAAAA AAGTTGTGGA AGAAGTTTCT    3000

CAGGAGTTCA GCAAGCCTTT CCATCTATCT TCTATTTTAA AAGAATGTGA TTTATTGTTT    3060

TTATGAATAA AATATACCTC GTGTGTTTCT CAAAAAAAAA AAAAAAAAAA AAA           3113
```

(2) INFORMATION FOR SEQ ID NO:21:

(i) SEQUENCE CHARACTERISTICS:
        (A) LENGTH: 828 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:21:

```
Met Asp Lys Asp Leu Ser Gly Tyr Lys Gly Ser Thr Pro Thr Lys
1               5                   10                  15

Gly Ile Glu Asn Lys Ala Phe Asp Arg Asn Thr Glu Ser Leu Phe Glu
            20                  25                  30

Glu Leu Ser Ser Ala Gly Ser Gly Leu Ile Gly Asp Val Asp Glu Gly
```

```
                  35                  40                  45
Ala Asp Leu Leu Gly Met Gly Arg Glu Val Glu Asn Leu Ile Leu Glu
    50                  55                  60
Asn Thr Gln Leu Leu Glu Thr Lys Asn Ala Leu Asn Ile Val Lys Asn
 65                  70                  75                  80
Asp Leu Ile Ala Lys Val Asp Glu Leu Thr Cys Glu Lys Asp Val Leu
                 85                  90                  95
Gln Gly Glu Leu Glu Ala Val Lys Gln Ala Lys Leu Lys Leu Glu Glu
                100                 105                 110
Lys Asn Arg Glu Leu Glu Glu Leu Arg Lys Ala Arg Ala Glu Ala
            115                 120                 125
Glu Asp Ala Gly Gln Lys Ala Lys Asp Asp Asp Ser Asp Ile Pro
130                 135                 140
Thr Ala Gln Arg Lys Arg Phe Thr Arg Val Glu Met Ala Arg Val Leu
145                 150                 155                 160
Met Glu Arg Asn Gln Tyr Lys Glu Arg Leu Met Glu Leu Gln Glu Ala
                165                 170                 175
Val Arg Trp Thr Glu Met Ile Arg Ala Ser Arg Glu Asn Pro Ala Met
            180                 185                 190
Gln Glu Lys Lys Arg Ser Ser Ile Trp Gln Phe Phe Ser Arg Leu Phe
            195                 200                 205
Ser Ser Ser Ser Asn Thr Thr Lys Lys Pro Glu Pro Pro Val Asn Leu
210                 215                 220
Lys Tyr Asn Ala Pro Thr Ser His Val Thr Pro Ser Val Lys Lys Arg
225                 230                 235                 240
Ser Ser Thr Leu Ser Gln Leu Pro Gly Asp Lys Ser Lys Ala Phe Asp
                245                 250                 255
Phe Leu Ser Glu Glu Thr Glu Ala Ser Leu Ala Ser Arg Arg Glu Gln
            260                 265                 270
Lys Arg Glu Gln Tyr Arg Gln Val Lys Ala His Val Gln Lys Glu Asp
            275                 280                 285
Gly Arg Val Gln Ala Phe Gly Trp Ser Leu Pro Gln Lys Tyr Lys Gln
        290                 295                 300
Val Thr Asn Gly Gln Gly Glu Asn Lys Met Lys Asn Leu Pro Val Pro
305                 310                 315                 320
Val Tyr Leu Arg Pro Leu Asp Glu Lys Asp Thr Ser Met Lys Leu Trp
                325                 330                 335
Cys Ala Val Gly Val Asn Leu Ser Gly Gly Lys Thr Arg Asp Gly Gly
            340                 345                 350
Ser Val Val Gly Ala Ser Val Phe Tyr Lys Asp Val Ala Gly Leu Asp
        355                 360                 365
Thr Glu Gly Ser Lys Gln Arg Ser Ala Ser Gln Ser Ser Leu Asp Lys
    370                 375                 380
Leu Asp Gln Glu Leu Lys Glu Gln Gln Lys Glu Leu Lys Asn Gln Glu
385                 390                 395                 400
Glu Leu Ser Ser Leu Val Trp Ile Cys Thr Ser Thr His Ser Ala Thr
                405                 410                 415
Lys Val Leu Ile Ile Asp Ala Val Gln Pro Gly Asn Ile Leu Asp Ser
            420                 425                 430
Phe Thr Val Cys Asn Ser His Val Leu Cys Ile Ala Ser Val Pro Gly
        435                 440                 445
Ala Arg Glu Thr Asp Tyr Pro Ala Gly Glu Asp Leu Ser Glu Ser Gly
    450                 455                 460
```

Gln Val Asp Lys Ala Ser Leu Cys Gly Ser Met Thr Ser Asn Ser Ser
465                 470                 475                 480

Ala Glu Thr Asp Ser Leu Leu Gly Gly Ile Thr Val Val Gly Cys Ser
            485                 490                 495

Ala Glu Gly Val Thr Gly Ala Ala Thr Ser Pro Ser Thr Asn Gly Ala
                500                 505                 510

Ser Pro Val Met Asp Lys Pro Pro Glu Met Glu Ala Glu Asn Ser Glu
            515                 520                 525

Val Asp Glu Asn Val Pro Thr Ala Glu Glu Ala Thr Glu Ala Thr Glu
530                 535                 540

Gly Asn Ala Gly Ser Ala Glu Asp Thr Val Asp Ile Ser Gln Thr Gly
545                 550                 555                 560

Val Tyr Thr Glu His Val Phe Thr Asp Pro Leu Gly Val Gln Ile Pro
                565                 570                 575

Glu Asp Leu Ser Pro Val Tyr Gln Ser Ser Asn Asp Ser Asp Ala Tyr
                580                 585                 590

Lys Asp Gln Ile Ser Val Leu Pro Asn Glu Gln Asp Leu Val Arg Glu
                595                 600                 605

Glu Ala Gln Lys Met Ser Ser Leu Leu Pro Thr Met Trp Leu Gly Ala
610                 615                 620

Gln Asn Gly Cys Leu Tyr Val His Ser Ser Val Ala Gln Trp Arg Lys
625                 630                 635                 640

Cys Leu His Ser Ile Lys Leu Lys Asp Ser Ile Leu Ser Ile Val His
                645                 650                 655

Val Lys Gly Ile Val Leu Val Ala Leu Ala Asp Gly Thr Leu Ala Ile
                660                 665                 670

Phe His Arg Gly Val Asp Gly Gln Trp Asp Leu Ser Asn Tyr His Leu
            675                 680                 685

Leu Asp Leu Gly Arg Pro His His Ser Ile Arg Cys Met Thr Val Val
690                 695                 700

His Asp Lys Val Trp Cys Gly Tyr Arg Asn Lys Ile Tyr Val Val Gln
705                 710                 715                 720

Pro Lys Ala Met Lys Ile Glu Lys Ser Phe Asp Ala His Pro Arg Lys
            725                 730                 735

Glu Ser Gln Val Arg Gln Leu Ala Trp Val Gly Asp Gly Val Trp Val
            740                 745                 750

Ser Ile Arg Leu Asp Ser Thr Leu Arg Leu Tyr His Ala His Thr Tyr
            755                 760                 765

Gln His Leu Gln Asp Val Asp Ile Glu Pro Tyr Val Ser Lys Met Leu
            770                 775                 780

Gly Thr Gly Lys Leu Gly Phe Ser Phe Val Arg Ile Thr Ala Leu Met
785                 790                 795                 800

Val Ser Cys Asn Arg Leu Trp Val Gly Thr Gly Asn Gly Val Ile Ile
                805                 810                 815

Ser Ile Pro Leu Thr Glu Ser Lys Tyr Ile Phe Arg
                820                 825

(2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:22:

CNCGACTGCCT TAAAATGTAA ACCTGGAT                                            29

(2) INFORMATION FOR SEQ ID NO:23:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:23:

TNGCACTGGGA AAGTGATTGT GAGGAGTA                                            29

(2) INFORMATION FOR SEQ ID NO:24:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:24:

TNGTGCTGCCA AAGAACAGGA GCCTCAAA                                            29

(2) INFORMATION FOR SEQ ID NO:25:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:25:

CTGCTGCTCA TTTGTTCAAT AATGTCAAC                                            29

(2) INFORMATION FOR SEQ ID NO:26:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:26:

TNGCACTGTTG TCATGACGGC TTGGTCTC                                            29

(2) INFORMATION FOR SEQ ID NO:27:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:27:

ANAACAGAGCA GTCCAGAGGA AGAACATC                                             29

(2) INFORMATION FOR SEQ ID NO:28:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "oligonucleotide"

(xi) SEQUENCE DESCRIPTION: SEQ ID NO:28:

ANATGACCAGA TCCTCTCAGA AGATTTCC                                             29

(2) INFORMATION FOR SEQ ID NO:29:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "oligonucleotide"

(xi) SEQUENCE DESCRIPTION: SEQ ID NO:29:

TNCCAGTGCTT GGGCATGCAT GAAGGCTA                                             29

(2) INFORMATION FOR SEQ ID NO:30:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "oligonucleotide"

(xi) SEQUENCE DESCRIPTION: SEQ ID NO:30:

ANCAGCAAACT CTTCCTTTCG CTTGCTGC                                             29

(2) INFORMATION FOR SEQ ID NO:31:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "oligonucleotide"

(xi) SEQUENCE DESCRIPTION: SEQ ID NO:31:

TNTTTCTCACA GGTCAGTTCA TCCACTTT                                             29

(2) INFORMATION FOR SEQ ID NO:32:

(i) SEQUENCE CHARACTERISTICS:
                (A) LENGTH: 1035 base pairs
                (B) TYPE: nucleic acid
                (C) STRANDEDNESS: double
                (D) TOPOLOGY: linear (ii) MOLECULE TYPE: cDNA (xi) SEQUENCE DESCRIPTION: SEQ ID NO:32:

```
AATCTTTTTG TTGTCAAGCT TGAGGTGTGG CAGGCTTGAG ATCTGGCCAT ACACTTGAGT      60
GACAATGACA TCCACTTTGC CTTTCTCTCC ACAGGTGTCC ACTCCCAGGT CCAACTGCAG     120
ACTTCGAATT CGGCCTTCAT GGCCTAGATG ATTGCAAGTC AATGGAAGGA GCTGCAGAGG     180
CAAATCAAAC GGCAGCACAG CTGGATTCTC AGGGCTCTGG ATACCATCAA AGCCGAGATA     240
CTGGCTACTG ATGTGTCTGT GGAGGATGAG GAAGGGACTG GAAGCCCCAA GGCTGAGGTT     300
CAACTATGCT ACCTGGAAGC ACAAAGAGAT GCTGTTGAGC AGATGTCCCT CAAGCTGTRC     360
AGCGAGCAGT ATACCAGCAG CAGCAAGCGA AAGGAAGAGT TTGCTGATAT GTCAAAAGTT     420
TCATTCAGTG GGAAGCAATG GGCTTCTGGA CTTTGATTCA GAATATCMGG AGCTCTGGGA     480
TTGGCTGATT GACATGGAGT CCCTTGTGAT GGACAGCCAC GACCTGATGA TGTCAGAGGA     540
GCAGCAGCAG CATCTTTACA AGCGATACAG TGTGGAAATG TCCATCAGAC ACCTGAAAAA     600
GACGGAGCTG CTTAGTAAGG TTGAAGCTTT GAAGAAAGGT GGCGTTTTAC TACCAAATGA     660
TCTCCTTGAA AAAGTGGATT CAATTAATGA AAAATGGGAA CTRCTTGGGG TATTTGCATT     720
TTTATTACTG TTTGTAGGTT ATGTGTACAT TTTTTGCGTA GTGAAGTACT CTGTCCGATT     780
TCTAATTTGA GGCACAAATA TCTCTCTCTT TCAATTCACT ACCTACGTTT CAAACAAGCT     840
ATTCATGCTA TTATGGGAAA GACACTGCTT TTCCTCTTCT GTTGATTTTT TTTTTTTCTG     900
AGCTTGTCCC CTCTCAGATT TTAATAATTT TGGTTCTTTA ATACATGAAA AGTAAGTAA     960
AATATGCCAT GTATTATGGG TATGCACCAA GTCAACTATA ATACAGTATA TCTGATATAT    1020
AAAAAAAAAA AAAAA                                                     1035
```

(2) INFORMATION FOR SEQ ID NO:33:

(i) SEQUENCE CHARACTERISTICS:
        (A) LENGTH: 179 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:33:

```
Met Cys Leu Trp Arg Met Arg Lys Gly Leu Glu Ala Pro Arg Leu Arg
1               5                   10                  15

Phe Asn Tyr Ala Thr Trp Lys His Lys Glu Met Leu Leu Ser Arg Cys
            20                  25                  30

Pro Ser Ser Cys Xaa Ala Ser Ser Ile Pro Ala Ala Ser Glu Arg
        35                  40                  45

Lys Ser Leu Leu Ile Cys Gln Lys Phe His Ser Val Gly Ser Asn Gly
    50                  55                  60

Leu Leu Asp Phe Asp Ser Glu Tyr Xaa Glu Leu Trp Asp Trp Leu Ile
65                  70                  75                  80

Asp Met Glu Ser Leu Val Met Asp Ser His Asp Leu Met Met Ser Glu
                85                  90                  95

Glu Gln Gln Gln His Leu Tyr Lys Arg Tyr Ser Val Glu Met Ser Ile
            100                 105                 110

Arg His Leu Lys Lys Thr Glu Leu Leu Ser Lys Val Glu Ala Leu Lys
        115                 120                 125

Lys Gly Gly Val Leu Leu Pro Asn Asp Leu Leu Glu Lys Val Asp Ser
    130                 135                 140

Ile Asn Glu Lys Trp Glu Leu Leu Gly Val Phe Ala Phe Leu Leu Leu
145                 150                 155                 160
```

```
Phe Val Gly Tyr Val Tyr Ile Phe Cys Val Val Lys Tyr Ser Val Arg
            165                 170                 175
Phe Leu Ile
```